(12) United States Patent
Nordlund et al.

(10) Patent No.: US 7,960,140 B2
(45) Date of Patent: Jun. 14, 2011

(54) AVIDIN MUTANTS

(75) Inventors: Henri Rainer Nordlund, Lempäälä (FI); Olli Heikki Laitinen, Pirkkala (FI); Vesa Pekka Hytönen, Ruutana (FI); Markku Sakari Kulomaa, Tampere (FI)

(73) Assignee: Orion Diagnostica Oy, Espoo (FI)

( * ) Notice: Subject to any disclaimer, the term of this patent is extended or adjusted under 35 U.S.C. 154(b) by 1152 days.

(21) Appl. No.: 10/579,393

(22) PCT Filed: Nov. 15, 2004

(86) PCT No.: PCT/FI2004/000679
§ 371 (c)(1),
(2), (4) Date: Aug. 15, 2006

(87) PCT Pub. No.: WO2005/047317
PCT Pub. Date: May 26, 2005

(65) Prior Publication Data
US 2009/0023185 A1  Jan. 22, 2009

(30) Foreign Application Priority Data

Nov. 14, 2003 (FI) .................................. 20031663

(51) Int. Cl.
*C12P 21/06* (2006.01)
*C07K 1/00* (2006.01)
*C07H 21/02* (2006.01)
(52) U.S. Cl. .................. 435/69.1; 435/320.1; 530/350; 536/23.1
(58) Field of Classification Search .................. 530/350; 536/23.1
See application file for complete search history.

(56) References Cited

U.S. PATENT DOCUMENTS
6,492,492 B1  12/2002  Slayton

*Primary Examiner* — Maryam Monshipouri
(74) *Attorney, Agent, or Firm* — Young & Thompson

(57) ABSTRACT

Two circularly permuted avidin monomers are designed. The circularly permuted monomers are fused and the resulting fusion peptides (dcAvd) form a pseudo-tetrameric dual-chain avidin, which is biologically active in biotin binding and shows similar structural characteristics as wild-type avidin. The dcAvd makes the development of dual-affinity avidins possible by allowing the adjustment of the ligand binding properties in the half of the binding sites differently than in the rest of the sites. The present invention provides further a single-chain avidin (scAvd) where two dcAvd-molecules are fused together via a linker to form a single polypeptide with four binding sites for biotin or other ligand.

19 Claims, 18 Drawing Sheets

```
                    Signal sequence
       ---------------------------------
       MVHATSPLLL  LLLLSLALVA  PGLSARKRTQ
              β5                  β6
            ------->             ------->
       PTFGFTVNWK  FSESTTVFTG  QCFIDRNGKE
              β7                    β8
            ------->               ------->
       VLKTMWLLRS  SVNDIGDDWK  ATRVGINIFT
                                    β1
                                 ------->
       RLRTQKEGGS  GGSARKCSLT  GKWTNDLGSN
        β2            β3
       ------>      ------->
       MTIGAVNSRG  EFTGTYITAV  TATSNEIKES
           β4             β6
         ------>         ------->
       PLHGTQNTIN  KSGGSTTVFT  GQCFIDRNGK
              β7                    β8
            ------->               ------->
       EVLKTMWLLR  SSVNDIGDDW  KATRVGINIF
                                    β1
                                 ------->
       TRLRTQKEGG  SGGSARKCSL  TGKWTNDLGS
         β2            β3
        ------>      ------->
       NMTIGAVNSR  GEFTGTYITA  VTATSNEIKE
            β4           β5
          ------>       ------->
       SPLHGTQNTI  NKRTQPTFGF  TVNWKFSE
```

B

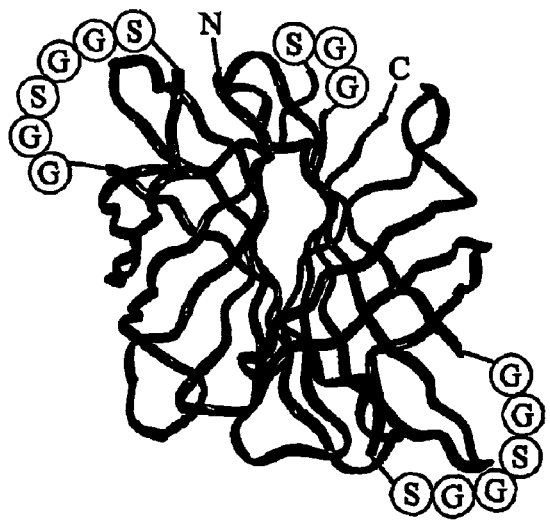

Fig. 6

ATGGTGCACGCAACCTCCCCGCTGCTGCTGCTGCT
GCTCAGCCTGGCTCTGGTGGCTCCCGGCCTCTGCCA
GGAAGAGGACCCAGCCCACCTTTGGCTTCACCGTCAAT
TGGAAGTTTTCAGAGTCCACCACTGTCTTCACGGGCCA
GTGCTTCATAGACAGGAATGGGAAGGAGGTCCTGAAG
ACCATGTGGCTGCTGCGGTCAAGTGTTAATGACATTGG
TGATGACTGGAAAGCTACCAGGGTCGGCATCAACATC
TTCACTCGCCTGCGCACACAGAAGGAGGGAGGCTCCG
GAGGCTCCGCCAGAAAGTGCTCGCTGACTGGGAAATG
GACCAACGATCTGGGCTCCAACATGACCATCGGGGCT
GTGAACAGCAGAGGTGAATTCACAGGCACCTACATCA
CAGCCGTAACAGCCACATCAAATGAGATCAAAGAGTC
ACCACTGCATGGGACACAAAACACCATCAACAAGTCC
GGCGGATCCACCACTGTCTTCACGGGCCAGTGCTTCAT
AGACAGGAATGGGAAGGAGGTCCTGAAGACCATGTGG
CTGCTGCGGTCAAGTGTTAATGACATTGGTGATGACTG
GAAAGCTACCAGGGTCGGCATCAACATCTTCACTCGCC
TGCGCACACAGAAGGAGGGAGGCTCCGGAGGCTCCGC
CAGAAAGTGCTCGCTGACTGGGAAATGGACCAACGAT
CTGGGCTCCAACATGACCATCGGGGCTGTGAACAGCA
GAGGTGAATTCACAGGCACCTACATCACAGCCGTAAC
AGCCACATCAAATGAGATCAAAGAGTCACCACTGCAT
GGGACACAAAACACCATCAACAAGAGGACCCAGCCCA
CCTTTGGCTTCACCGTCAATTGGAAGTTTTCAGAGGGA
GGTTCCGGATCGGGATCCGGCTCTGGCAGCGGCAGGA
CCCAGCCCACCTTTGGCTTCACCGTCAATTGGAAGTTT
TCAGAGTCCACCACTGTCTTCACGGGCCAGTGCTTCAT
AGACAGGAATGGGAAGGAGGTCCTGAAGACCATGTGG
CTGCTGCGGTCAAGTGTTAATGACATTGGTGATGACTG
GAAAGCTACCAGGGTCGGCATCAACATCTTCACTCGCC
TGCGCACACAGAAGGAGGGAGGCTCCGGAGGCTCCGC
CAGAAAGTGCTCGCTGACTGGGAAATGGACCAACGAT
CTGGGCTCCAACATGACCATCGGGGCTGTGAACAGCA
GAGGTGAATTCACAGGCACCTACATCACAGCCGTAAC
AGCCACATCAAATGAGATCAAAGAGTCACCACTGCAT
GGGACACAAAACACCATCAACAAGTCCGGCGGATCCA
CCACTGTCTTCACGGGCCAGTGCTTCATAGACAGGAAT
GGGAAGGAGGTCCTGAAGACCATGTGGCTGCTGCGGT
CAAGTGTTAATGACATTGGTGATGACTGGAAAGCTAC
CAGGGTCGGCATCAACATCTTCACTCGCCTGCGCACAC
AGAAGGAGGGAGGCTCCGGAGGCTCCGCCAGAAAGTG
CTCGCTGACTGGGAAATGGACCAACGATCTGGGCTCC
AACATGACCATCGGGGCTGTGAACAGCAGAGGTGAAT
TCACAGGCACCTACATCACAGCCGTAACAGCCACATC
AAATGAGATCAAAGAGTCACCACTGCATGGGACACAA
AACACCATCAACAAGAGGACCCAGCCCACCTTTGGCT
TCACCGTCAATTGGAAGTTTTCAGAGTGA

Fig. 7

ATGGTGCACGCAACCTCCCCGCTGCTGCTGCTGCTGCTCA
GCCTGGCTCTGGTGGCTCCCGGCCTCTCTGCCAGGAAGAGGAC
CCAGCCCACCTTTGGCTTCACCGTCAATTGGAAGTTTTCAGAG
TCCACCACTGTCTTCACGGGCCAGTGCTTCATAGACAGGAATG
GGAAGGAGGTCCTGAAGACCATGTGGCTGCTGCGGTCAAGTGT
TAATGACATTGGTGATGACTGGAAAGCTACCAGGGTCGGCATC
AACATCTTCACTCGCCTGCGCACACAGAAGGAGGGAGGCTCCG
GAGGCTCCGCCAGAAAGTGCTCGCTGACTGGGAAATGGACCAA
CGATCTGGCTCCAACATGACCATCGGGGCTGTGAACAGCAGA
GGTGAATTCACAGGCACCTACATCACAGCCGTAACAGCCACAT
CAAATGAGATCAAAGAGTCACCACTGCATGGGACACAAAACAC
CATCAACAAGTCCGGCGGATCCACCACTGTCTTCACGGGCCAG
TGCTTCATAGACAGGAATGGGAAGGAGGTCCTGAAGACCATGT
GGCTGCTGCGGTCAAGTGTTAATGACATTGGTGATGACTGGAA
AGCTACCAGGGTCGGCATCAACATCTTCACTCGCCTGCGCACA
CAGAAGGAGGGAGGCTCCGGAGGCTCCGCCAGAAAGTGCTCGC
TGACTGGGAAATGGACCAACGATCTGGCTCCAACATGACCAT
CGGGGCTGTGAACAGCAGAGGTGAATTCACAGGCACCTACATC
ACAGCCGTAACAGCCACATCAAATGAGATCAAAGAGTCACCAC
TGCATGGGACACAAAACACCATCAACAAGAGGACCCAGCCCAC
CTTTGGCTTCACCGTCAATTGGAAGTTTTCAGAGTGA

Fig. 17

```
1        MNKPSKFALP LAFAAVTASG VASAGTQPTF GFTVNWKFSE
STTVFTGQCF IDRNGKEVLK
61       TMWLLRSSVN DIGDDWKATR VGINIFTRLR TQKEGGSGGS
ARKCSLTGKW TNDLGSNMTI
121      GAVNSRGEFT GTYITAVTAT SNEIKESPLH GTQNTINKSG
GSKESPLHGT QNTINKRTQP
181      TFGFTVNWKF SESTTVFTGQ CFIDRNGKEV LKTMWLLRSS
VNDIGDDWKA TRVGINIFTR
241      LRTQKEGGSG GSARKCSLTG KWTNDLGSNM TIGAVNSRGE
         FTGTYITAVT
```

Fig. 18

```
1        ATGAACAAAC CCTCCAAATT CGCTCTGCCG CTTGCCTTCG
CCGCCGTTAC GGCCTCTGGT
61       GTTGCCTCGG CTGGTACCCA GCCCACCTTT GGCTTCACCG
TCAATTGGAA GTTTTCAGAG
121      TCCACCACTG TCTTCACGGG CCAGTGCTTC ATAGACAGGA
ATGGGAAGGA GGTCCTGAAG
181      ACCATGTGGC TGCTGCGGTC AAGTGTTAAT GACATTGGTG
ATGACTGGAA AGCTACCAGG
241      GTCGGCATCA ACATCTTCAC TCGCCTGCGC ACACAGAAGG
AGGGAGGCTC CGGAGGCTCC
301      GCCAGAAAGT GCTCGCTGAC TGGGAAATGG ACCAACGATC
TGGGCTCCAA CATGACCATC
361      GGGGCTGTGA ACAGCAGAGG TGAATTCACA GGCACCTACA
TCACAGCCGT AACAGCCACA
421      TCAAATGAGA TCAAAGAGTC ACCACTGCAT GGGACACAAA
ACACCATCAA CAAGTCCGGC
481      GGATCCAAAG AGTCACCACT GCATGGGACA CAAAACACCA
TCAACAAGAG GACCCAGCCC
541      ACCTTTGGCT TCACCGTCAA TTGGAAGTTT TCAGAGTCCA
CCACTGTCTT CACGGGCCAG
601      TGCTTCATAG ACAGGAATGG GAAGGAGGTC CTGAAGACCA
TGTGGCTGCT GCGGTCAAGT
661      GTTAATGACA TTGGTGATGA CTGGAAAGCT ACCAGGGTCG
GCATCAACAT CTTCACTCGC
721      CTGCGCACAC AGAAGGAGGG AGGCTCCGGA GGCTCCGCCA
GAAAGTGCTC GCTGACTGGG
781      AAATGGACCA ACGATCTGGG CTCCAACATG ACCATCGGGG
CTGTGAACAG CAGAGGTGAA
841      TTCACAGGCA CCTACATCAC AGCCGTAACA TAA
```

AVIDIN MUTANTS

This application is the National Stage entry of PCT/FI2004/000679, filed Nov. 15, 2004, which claims foreign priority to Finnish application 20031663, filed Nov. 14, 2003.

FIELD OF THE INVENTION

The present invention is in the field of modified avidin, and more particularly in the area of avidin fusion proteins wherein two circularly permuted avidin monomers were fused to a dual-chain avidin (dcAvd) leading to a dual-chain pseudo-tetrameric avidin containing two polypeptides instead of four in the native protein. The present invention provides further a single-chain avidin (scAvd) where two dcAvd-molecules are fused together via a linker to form a single polypeptide with four binding sites for biotin.

BACKGROUND OF THE INVENTION

Avidin, a glycoprotein found in chicken egg white as well as its distant relative, streptavidin from *Streptomyces* bacteria (Argarana, C. E. et al. Nucleic Acids Res 14, 1871-82 (1986)), have high affinity for biotin. This firm interaction has been utilized in countless applications in the different fields of life sciences to probe, label and affinity separate biomolecules. Another premise for the system has been the easy coupling of biotin to almost any other molecules without compromising the strong (strept)avidin-biotin bond or the function of the coupled molecule (Green, M. N. Advances in Protein Chemistry 29, 85-133 (1975), Wilchek, M. & Bayer, E. A. Biomol Eng 16, 1-4 (1999)).

Avidin is a homotetramer encoded by a single gene (Ahlroth, M. K. et al. Anim Genet 31, 367-75 (2000), Wales, M. J. et al. Gene 161, 205-9 (1995)). This fact together with the almost perfect 222 point structural symmetry (Pugliese, L. et al. Journal of Molecular Biology 231, 698-710 (1993)) and the orientation of the subunits in the protein guarantees that all four biotin-binding sites in avidin have equally high affinity towards biotin. From the evolutional point of view this also means that in the protein all four binding sites co-evolve. The monomers of avidin are simple classical up-and-down β-barrel proteins. They have identical topology of eight β-strands and their interconnecting loops (Pugliese, L. et al. Journal of Molecular Biology 231, 698-710 (1993), Hendrickson, W. A. et al. Proceedings of The National Academy of Sciences of the United States of America 86, 2190-2194 (1989), Livnah, O. et al. Proceedings of The National Academy of Sciences of the United States of America 90, 5076-5080 (1993)). If the 3-D structure of avidin is superimposed with that of streptavidin it is evident that the termini and also the biotin-binding pocket situates in topologically analogous regions in these proteins. Two monomer pairs in each avidin tetramer share a large common interface and they are therefore called as the structural dimers. The complete tetramer is composed of two of such structural dimers (Pugliese, L. et al. Journal of Molecular Biology 231, 698-710 (1993), Hendrickson, W. A. et al. Proceedings of The National Academy of Sciences of the United States of America 86, 2190-2194 (1989), Livnah, O. et al. Proceedings of The National Academy of Sciences of the United States of America 90, 5076-5080 (1993), Weber, P. C. et al. Science 243, 85-88 (1989)).

During the recent years avidin and streptavidin have been engineered via site-directed mutagenesis (Laitinen, O. H. et al. J Biol Chem 276, 8219-24 (2001), Laitinen, O. H. et al. FEBS Lett 461, 52-8 (1999), Marttila, A. T. et al. FEBS Lett 441, 313-7 (1998), Marttila, A. T. et al. FEBS Lett 467, 31-6 (2000), Reznik, G. O. et al. Proceedings of The National Academy of Sciences of the United States of America 95, 13525-30 (1998), Reznik, G. O. et al. Nat Biotechnol 14, 1007-11 (1996), Sano, T. et al. Proceedings of The National Academy of Sciences of the United States of America 94, 6153-6158 (1997), Sano, T. & Cantor, C. R. Proceedings of The National Academy of Sciences of the United States of America 92, 3180-3184 (1995), Chilkoti, A. et al. Bio/Technology 13, 1198-1204 (1995), Chilkoti, A. et al. Proceedings of The National Academy of Sciences of the United States of America 92, 1754-1758 (1995). Chu, V. et al. Protein Sci 7, 848-59 (1998), Freitag, S. et al. Proceedings of The National Academy of Sciences of the United States of America 96, 8384-9 (1999), McDevitt, T. C. et al. Biotechnol Prog 15, 391-6 (1999)). In some studies the focus has been on the adjustment of the physico-chemical properties of (strept)avidin whereas in other studies the target has been on the fine-tuning of the biotin-binding affinity. Nevertheless, as these mutant protein subunits are single gene products the desired changes, produced by mutations, take effect in all (strept) avidin subunits concurrently.

In several cases, however, it would be beneficial to alter for example the binding-affinity only in some subunits of the tetramer while conserving the tight binding in the rest of the binding sites. Chilkoti et al. have introduced a partial solution to this problem by producing separately two streptavidin forms, one having natural high-affinity biotin-binding capacity and another with reduced affinity (Chilkoti, A. et al. Bio/Technology 13, 1198-1204 (1995)). They denaturated these two forms and mixed them, after which the mixture was renatured. Nonetheless, the refolding led to many alternative forms: some of them contained four high affinity binding sites whereas other forms had a raising series of lower affinity binding sites, finally ending in the form that contained four lower affinity binding sites. In this sense the genetic fusion of the subunits might be more straightforward and effective strategy to create (strept)avidin molecules containing biotin-binding sites of variable affinity because it would lead into the uncoupling of the monomers as an evolutionary and protein engineering unit and therefore production of better quality preparations. The N- and C-termini of the distinct (strept) avidin subunits are, however, situated far away from each other in the quaternary structure and therefore it is presumable that any simple fusion strategy would fail.

A common approach to study protein folding and significance of secondary structure topology to the protein structure and function is the creation of circularly permuted forms of the examined proteins (Uliel et al. Protein Eng 14, 533-542 (2001)). Creation of circular permutations is an approach wherein the normal termini of a polypeptide are linked and new termini are created by breaking the backbone elsewhere. In many polypeptides, the normal termini are in close proximity and can be joined by a short amino acid sequence. The break in the polypeptide backbone can be at any point, preferably at a point where the natural function and folding of the polypeptide are not destroyed. In most cases proteins stand the circular permutations considerably well without exhibiting radical alterations in their structures or functions. Following circular permutation new C- and N-termini are created to the protein, allowing creation of fusion proteins wherein the fused peptide or protein is attached at a different place on the host protein.

Usually in this approach the original N- and C-termini are joined together with a linker peptide whereas the new termini are typically introduced into loop regions. Chu et al. have described a circularly permuted streptavidin that showed almost identical 3-D structure when compared to that of the native protein (Chu et al. Protein Sci 7, 848-59 (1998)). In that study the circular permutation strategy was used as a tool to delete the loop between α-strands three and four in streptavidin monomers. This loop is functionally important because it undergoes the open to closed conformational change upon biotin binding (Hendrickson et al. Proceedings of The National Academy of Sciences of the United States of America 86, 2190-2194 (1989), Weber et al. Science 243, 85-88 (1989)). Consequently, when the new termini were introduced in this loop, the affinity of the resultant mutant for biotin collapsed six orders of magnitude as compared to the wild-type (wt) streptavidin.

In U.S. Pat. No. 6,492,492 circularly permuted streptavidins were designed by altering one monomer but the monomers were not fused together. The resulting streptavidin has four monomers as the wt protein.

BRIEF SUMMARY OF THE INVENTION

The objective of the present invention is to create a dual-chain mutant avidin with four binding sites that would consist of only two polypeptide chains. Another objective of the present invention is to provide a single-chain avidin where two dual-chain avidin molecules are fused together to form a single polypeptide with four binding sites for biotin. Another objective was to generate avidins in which the neighbouring biotin-binding sites of dual chain avidin exhibit two different affinities for biotin. Still another objective was to generate dual chain and single chain avidins in which at least one biotin binding site binds ligands other than biotin.

Two circularly permuted chicken avidin monomers were designed in aim to fuse them and produce a fusion avidin containing two polypeptides instead of four in the native protein. First, two circularly permuted avidin monomers (cpAvd5→4 and cpAvd6→5) were constructed, wherein the new termini were in an ideal position to allow the building of the desired genetic fusion. The construction of this dual-chain avidin (dcAvd) by fusing the monomers of the structural dimer together is described and it is shown that it forms wild type (wt) like pseudo-tetrameric quaternary structure and that its four biotin-binding sites exhibit high-affinity biotin binding. Therefore this construct is useful as a structural scaffold to change the affinity parameters in some subunits while preserving the high biotin-binding affinity in the remaining binding sites. The circularly permuted avidin monomers (cpAvd5→4 and cpAvd6→5) could be further mutagenized by site specific mutagenesis before fusion.

In single-chain avidin two dual-chain avidin molecules are fused together via a linker to form a single polypeptide with four binding sites for biotin. Each of the four binding sites can be modified by protein engineering independently.

Avidins were generated in which the neighbouring biotin-binding sites of dual chain avidin exhibit two different affinities for biotin. In these novel avidins, one of the two binding sites in each polypeptide chain, the pseudodimer, is genetically modified to have lower binding affinity for biotin, whereas the remaining binding site still exhibits the high affinity characteristic of the wild-type protein. The pseudotetramer, i.e. a dimer of dual chain avidins, has two high and two lower affinity biotin-binding sites. These "dual-affinity" avidin molecules open up wholly new possibilities in avidin-biotin technology, where they may have uses as a novel bioseparation tools, carrier proteins or nanoscale adapters.

In the circularly permuted avidins the natural termini of the polypeptide monomer are joined and the protein is opened at another point to create new C- and N-termini. The changed locations of the new N- and C-termini in the circularly permuted avidin monomer enable the creation of the fusion construct in which a short spacer peptide joins the two subunits. The original N- and C-termini of the wild-type avidin are connected to each other via glysine/serine rich linker. The circularly permuted avidin monomers are fused and the resulting fusion peptides (dcAvd) form a pseudo-tetrameric dual-chain avidin, which is biologically active in the sense of biotin binding and shows similar structural characteristics as wild-type avidin. The dcAvd described in the present study makes the development of dual-affinity avidins possible by allowing the adjustment of the ligand binding properties in the half of the binding sites while enabling the conserved affinity in the rest of the sites.

BRIEF DESCRIPTION OF THE DRAWINGS

FIG. 1. (A) The amino acid sequence of the two fused monomers of avidin (dcAvd) (SEQ ID NO:2) with the locations of the wt β-strands indicated. The underlined ARK denotes the three first amino acids of wt avidin (SEQ ID NO:1). The artificial linkers GGSGGS (SEQ ID NO:3) and the monomer-monomer transition spacer SGG are highlighted with boxes. The part that is derived from cpAvd5→4 is underlined with the first bar and the part derived from cpAvd6→5 is underlined with the second bar. (B) Schematic illustration of the fused monomers of the wt structural dimer in dcAvd. The artificial linkers (GGSGGS) (SEQ ID NO: 3) that connect the original termini and the intermonomeric spacer (SGG) are circled. The left part is derived from cpAvd5→4 and the right part is derived from cpAvd6→5.

FIG. 6. DNA sequence which codes for scAvd of SEQ ID NO: 24. For said DNA sequence also SEQ ID NO: 25 is provided in the Sequence Listing.

FIG. 7. DNA sequence which codes for dcAvd of SEQ ID NO: 2. For said DNA sequence also SEQ ID NO: 26 is provided in the Sequence Listing.

FIG. 17. Dual chain avidin dcAvd54+43 amino acid sequence (SEQ ID NO:28). The signal peptide is underlined as well as the peptide linkers between N- and C-terminus of circularly permuted avidins and the SGGS (SEQ ID NO: 30) linker connecting 5→4 and 4→3 avidins.

FIG. 18. Dual chain avidin dcAvd54+43 DNA sequence (SEQ ID NO:29).

DETAILED DESCRIPTION OF THE INVENTION

Figure 2:
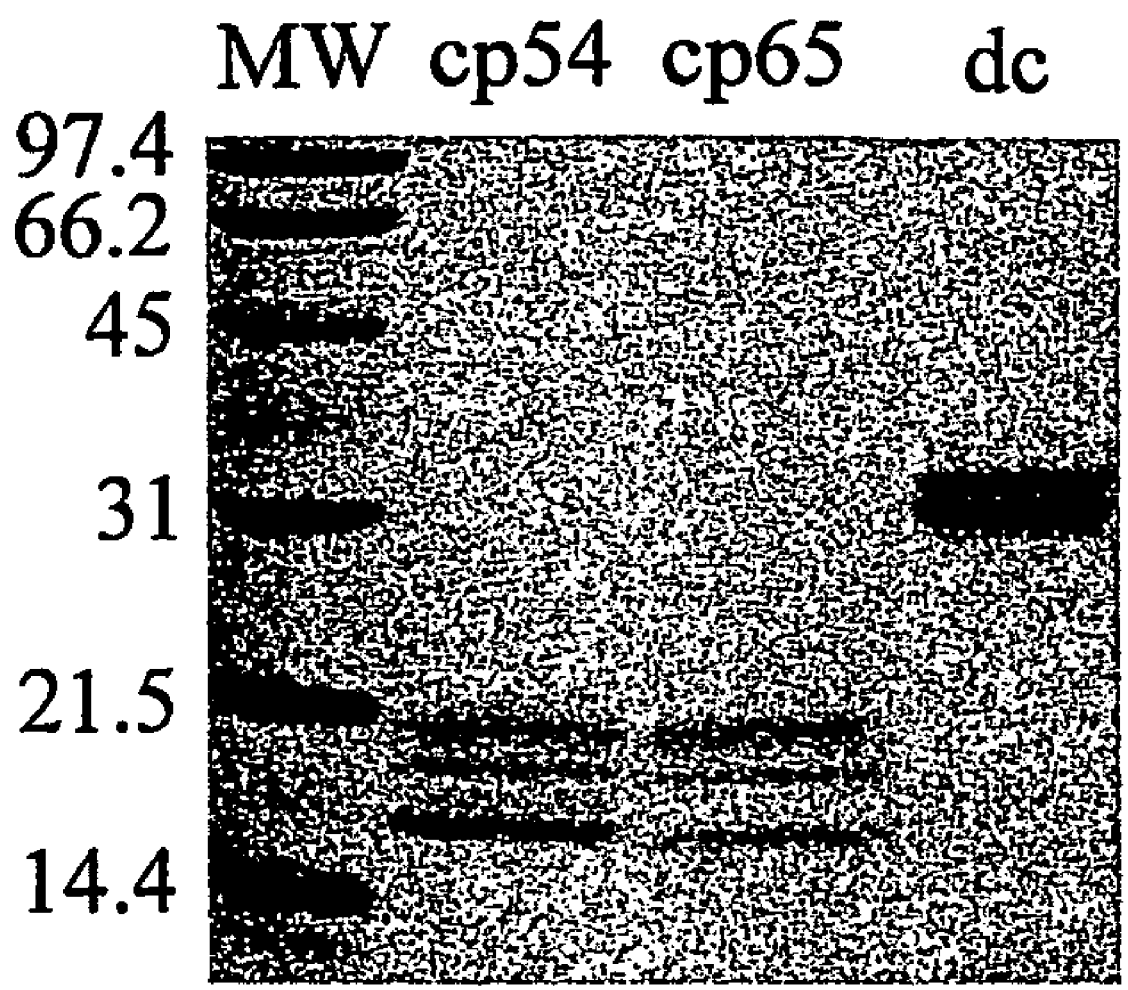
FIG. 2. Denaturing SDS-PAGE analysis confirmed that the size of the fused monomers present in the dcAvd is twice of that compared to the size of the circularly permuted avidin monomers cpAvd5→4 (cp54) and cpAvd6→5 (cp65). The unit of the molecular weight (MW) is kDa.

There are two main reasons why there exist so many studies describing different chemical modifications and multiple genetically engineered mutants of avidin and streptavidin: the first motive is naturally connected to the colossal utilization of these proteins in a legion of applications. Therefore their physico-chemical properties and the biotin-binding properties have been regulated in aim to broaden the spectrum of applications and conditions wherein they can be used as well as to decrease some drawbacks that (strep)avidin-biotin system has. On the other hand, (strep)avidin-biotin pair offers for the scientist an interesting model system to study the structure and/or function related issues.

In the present application avidin-biotin complex was used as a model to radically engineer the topology of the multisubunit protein, whose N- and C-termini in distinct subunits are far away from each other, and do that so that the resultant avidin with four binding sites would be composed of two polypeptide chains. The task was accomplished by joining the two monomers that form the structural dimer in the wt avidin together. The resultant protein should maintain its structurally and functionally important properties as close as possible to the wt protein. Sanders et al. (Sanders, K. E., Lo, J., & Sligar, S. G., Blood 100, 299-305 (2002)) have succeeded to make such a maneuver when they first constructed circular permutant of the α-chain of hemoglobin and in the subsequent step they fused this novel subunit to the native α-unit. This fused pseudo-dimeric α-unit was able to oligomerize with the wt β-subunits and the resultant oligomer was functional in a way almost indistinguishable from the wt oligomer. However this case was different when compared to the dual-chain avidin described in this application: only two subunits of the heterotetrameric complex were joined to single polypeptide chain and two other entered the complex as single units.

All the amino acid residues referred with number in the following text refer to the amino acids in modified avidins corresponding the structurally analogous amino acid residues in the chicken avidin (Livnah, O. et al. Proceedings of The National Academy of Sciences of the United States of America 90, 5076-5080 (1993)).

The natural topology of the wt avidin was modulated in order to arrange the termini of the subunits closer to each other. First two circularly permuted avidin monomers were constructed so that in the first mutant the termini were in the one end of the barrel whereas in the second mutant they situated in the opposite end. Because biotin binds to one end of the avidin barrel one could foresee that in the circularly permuted avidin monomer, cpAvd6→5, where the new termini were introduced in that end it could affect the biotin binding. In cpAvd6→5 the new N-terminus is before β-strand 6 and new C-terminus after β-strand 5. In cpAvd6→5, where the new termini appeared to the loop between the α-strands 5 and 6 containing biotin-binding residues Trp70, Phe72 Ser73 and Ser75 (numbering according to wt avidin (Livnah, O. et al. Proceedings of The National Academy of Sciences of the United States of America 90, 5076-5080 (1993))), the biotin-binding activity was reduced. One reason for the lowered affinity might be that the new free termini and therefore also these biotin-binding residues have more freedom to move compared to the corresponding loop in wt protein. When judged against previously mentioned circularly permuted streptavidin (Chu, V. et al. Protein Sci 7, 848-59 (1998)) the affinity of cpAvd6→5 was, however, preserved relatively well. Instead in cpAvd5→4 where the new termini were introduced to the loop between the β-strands 4 and 5, which situates in the 3D-structure at the non-binding end of the barrel, no major changes were detected in its biotin-binding properties. In cpAvd5→4 the new N-terminus is before α-strand 5 and new C-terminus after α-strand 4.

The difference between the biotin-binding affinity, or other ligand-binding affinity, such as HABA, of the circularly permuted avidin and the wild type avidin ligand-binding affinity is at least 5-fold more or less, preferably the difference is 10-fold, more preferably 100-fold and most preferably 1000-fold.

Interestingly, the dual-chain avidin (dcAvd) exhibited binding properties, which were somewhere between these two circularly permuted forms. One apparent reason for that is the fact, that the dcAvd pseudo-tetramer has two considerably well preserved biotin-binding sites exhibiting strong affinity towards biotin originated from the cpAvd5→4 part and two biotin-binding sites with moderate affinity originated from the cpAvd6→5. On the other hand, in dcAvd two of the new termini have been fused with the SGG spacer, which provides the transition from one monomer to the other. In this case it may rescue part of the structural stability of the wild-type loop (5→6) and therefore also restore part of the binding affinity.

The thermal stability and proteinase K durability of the circularly permuted avidin monomers and dual chain avidin was somewhat lower than that of the wild type avidin. Proteinase K seemed to digest the new loops faster (not shown) than the loop 3-4 that it is capable to break in the wt avidin (Ellison, D. et al. *Protein Sci* 4, 1337-45 (1995)). As cpAvd6→5 seemed to be more heavily glycosylated than cpAvd5→4 it may also explain why the molecular weight of the former mutant, according to HPLC, was slightly higher than that of the latter one.

Due to its structural symmetry the dual-chain avidin may result to two different quaternary structure assemblies. Depending on the outcome of this quaternary structure assembly the termini of both single-chain dimers may be orientated to the same or to the opposite directions in the pseudo-tetramer. From the applicative point of view the ideal position would be such that the functionally identical ends would point to the same direction. Then it is possible to develop a system wherein, for example, the tighter binding sites bind to biotin containing surface, whereas the lower affinity binding sites point to solution. It is, however, possible to introduce non-symmetrical disulphide bridges between the single-chain dimers in order to fix their quaternary structure to the desired assembly.

While the preferred embodiment is described herein as derived from wild type avidin, it should be apparent to those skilled in the art that the circularly permuted avidin monomers and fusion proteins described herein can be made with variations of wild type avidin. Unless otherwise indicated or unless otherwise clear from the context, the term avidin is intended to encompass all forms of avidin including wild type avidin, mutant forms of avidin, streptavidin and variants of avidin, such as other poultry avidins (Hytönen et al. (2003), Biochem J. 372(Pt 1):219-225, which is incorporated by reference) comprising avidin proteins isolated from duck, goose, ostrich and turkey (turkey avidin (partial sequence) GenBank accession number AAN38297.1), and chicken avidin-related proteins (AVRs) (WO 2004/018509 is included here as reference). The present invention could be applied even to other proteins, which bind biotin including bacterial streptavidin.

"Dual-chain avidin" means fusion of two circularly permutated avidins as defined above, which binds biotin and/or other ligand. In preferred embodiments dual-chain avidins form a pseudotetramer.

"Single-chain avidin" means fusion of two dual-chain avidins or fusion of four circularly permuted avidins as defined above.

Circularly permuted proteins generally are created by disrupting the polypeptide chain at a selected point to create new termini and bridging the two natural termini either directly or through a linker such as an amino acid linker. Circular permutation thus has the effect of essentially preserving the sequence and identity of the amino acids of a protein while generating new termini at different locations. Moreover, the tertiary structure of the protein is generally conserved.

There are two general requirements for the creation of a circularly permuted protein that retains its native biological activity: 1) the termini in the native protein must be favorably located so that creation of a linkage does not destroy biological activity; and 2) there must exist an "opening site" where new termini can be formed without disrupting a region critical for protein folding and desired biological activity. In some cases it is possible to modify biological activity, such as biotin binding in the case of avidin.

Generally, linkers are molecules that contain two reactive sites, one that will form a covalent bond with the carboxyl terminal amino acid and one that will form a covalent bond with the amino terminal amino acid. Suitable linkers are well known to those of skill in the art and include, but are not limited to, straight or branched-chain carbon linkers, heterocyclic carbon linkers, or peptide linkers. The most common and simple example is a peptide linker that consists of several amino acids joined through the peptide bonds to the termini of the native protein. The linkers may be joined to the terminal amino acids through their side groups. However, in a preferred embodiment, the linkers will be joined through peptide bonds to the alpha carbon amino and carboxyl groups of the terminal amino acids. Generally, neutral amino acids and/or amino acids with small side chains are preferred, such as glycine, alanine, and serine.

It is preferable to use a linker that preserves the spacing between the termini comparable to the unpermuted or native molecule, particularly if the desire is to maintain or improve the native biological activity of the molecule. For circularly permuted avidin, the linker is composed of several amino acids, preferably about one to six amino acids. Most preferably, the linker is a peptide of four glycine residues and two serine residue, in the order GGSGGS (SEQ ID NO:3). The first glycine is attached to the carboxyl terminal amino acid of the native protein and the serine is attached to the amino terminal amino acid of the native protein.

The selection of an opening site may be determined by a number of factors. One factor is whether the biological function is to be preserved or altered. If the biological function is not to be altered, the opening site should be away from the active site and away from other structurally or functionally important sites. For example, preferred opening sites will be located in regions that do not show a highly regular three-dimensional structure such as alpha helices, pleated sheets, β-barrel structures, and the like. However, if the object is to alter the biological function, it may be more advantageous to open the molecule near the active site. For example, to lower the biotin binding affinity of avidin, the opening site can be located on the flexible loop near the biotin binding site that contains amino acids that participate in biotin binding. In the present invention the opening site was situated between the β-sheets 4 and 5 in the first monomer and between the β-sheets and 6 in the second monomer. Furthermore, another dual-chain avidin is presented, in where the opening situates between the β-sheets 4 and 5 in the first monomer and between the β-sheets 3 and 4 in the second monomer.

The fusion proteins described herein includes two avidin monomers, which have been circularly permuted (cpAvd5→4 and cpAvd6→5 or cpAvd5→4 and cpAvd4→3). The two proteins may be fused together directly or joined by means of a spacer, such as a peptide spacer. The peptide spacer may range from about 1 to 40 residues in length, but also other spacers with alternative length or composition may be used. It is desirable to retain full or partial biological activity of both monomers. The length and characteristics of the spacer will be important in achieving this objective. Generally the spacer connecting the two monomers has no biological activity itself and functions only to link and provide some distance between the two active proteins forming the fusion protein. However, one of skill will recognize that the residues of the spacer may be chosen to optimise a property of the fusion protein. Here preferably a spacer of three amino acids, one serine and two glycine residues, is used (SGG).

The circularly permuted avidin monomers (cpAvd5→4 and cpAvd6→5 and cpAvd4→3) could be further mutagenized by site specific mutagenesis before fusion in order to construct dual-chain avidin monomers, which bear, for example, two different kinds of binding sites. Hence, the binding affinity or specificity in the two neighbouring binding sites in dual-chain avidin monomer can be different from each other. In the present invention the cpAvd5→4 and/or cpAvd6→5 derived parts of dcAvd were mutated. The monomer can be mutated by changing the tyrosine residue 33 to any other amino acid residue X and/or isoleucine residue 117 to any other amino acid residue X, (Y33X, I117X). Preferably the monomer can be mutated by changing the tyrosine residue 33 to histidine residue and/or the isoleucine residue 17 to cysteine residue, (Y33H, I117X). Owing to these modifications dcAvd mutant, p54(I117C)+p65(Y33H), contains two high-affinity binding sites and two low-affinity binding sites. Mutagenised amino acid residues in cpAvd molecules may also include serine 16 or threonine 35 or asparagine 118. Furthermore, residues can be omitted from the circularly permuted proteins. Here, for example, six residues were removed from the avidin sequence when cpAvd4→3 was created.

The circularly permuted proteins and fusion proteins may be made using methods known to those of skilled in the art. These include chemical synthesis, modifications of existing proteins, and expression of circularly permuted proteins using recombinant DNA methodology. The fusion protein can be made as a single polypeptide or the second peptide can be attached to the base polypeptide after separate synthesis of the two component polypeptides. The circularly permuted protein and/or fusion protein may be made by chemically modifying a native or preexisting protein. Generally, this requires reacting the native protein in the presence of the linker to form covalent bonds between the linker and the carboxyl and amino termini of the protein, thus forming a circular protein. New termini are then formed by opening the peptide bond joining amino acids at another location. This may be accomplished chemically or enzymatically using, for example, a peptidase.

In the preferred embodiment, the circularly permuted proteins, and/or fusion proteins including the circularly permuted proteins, will be synthesized using recombinant methodology. Generally, this involves creating a polynucleotide sequence that encodes the circularly permuted base polypeptide (or the entire fusion protein containing the base polypeptide), placing the polynucleotide in an expression cassette under the control of a suitable expression promoter, expressing the protein in a host, isolating the expressed protein and, if required, renaturing the protein. If the secondary protein is made separately it is then ligated to the circular permutant.

DNA encoding a circularly permuted polypeptide or fusion protein including the circularly permuted polypeptide can be prepared by any suitable method, including, for example, cloning and restriction of appropriate sequences or direct chemical synthesis by methods such as the phosphotriester method of Narang et al. Meth. Enzymol. 68: 90-99 (1979); the phosphodiester method of Brown et al., Meth. Enzymol. 68: 109-151 (1979); the diethylphosphoramidite method of Beaucage et al., Tetra. Lett., 22: 1859-1862 (1981); and the solid support method of U.S. Pat. No. 4,458,066. Alternatively, partial length sequences may be cloned and the appropriate partial length sequences cleaved using appropriate restriction enzymes. The fragments may then be ligated to produce the desired DNA sequence. In a preferred embodiment, DNA encoding the circularly permuted polypeptide will be produced using DNA amplification methods, for example polymerase chain reaction (PCR).

The circularly permuted proteins and their fusion proteins may be expressed in a variety of host cells, including *E. coli*, other bacterial hosts, yeast, and various higher eukaryotic cells, such as the COS, CHO and HeLa cells lines, insect cells, and myeloma cell lines, as well as in different plant production systems (corn, tobacco etc.) and in transgenic animals (rodent, bovine etc.). Even production in vitro could be profitable. In a preferred embodiment of the present invention the fusion protein is encoded by a plasmid or a viral vector. The recombinant protein gene is operable linked to appropriate expression control sequences for each host.

The DNA constructs encoding the circularly permuted proteins or fusion protein can be transferred to be expressed into the chosen host system by methods well known for those skilled in the art.

Once expressed, the recombinant base circularly permuted protein or fusion protein can be purified according to standard procedures of the art, including ammonium sulfate precipitation, affinity chromatography, gel electrophoresis and the like. Substantially pure compositions of at least about 90 to 95% homogeneity are preferred, and 98 to 99% or more homogeneity is most preferred for pharmaceutical uses. Once purified, partially or to homogeneity as desired, the polypeptides may then be used as desired.

After chemical synthesis, biological expression, or purification, the circularly permuted polypeptide and/or fusion protein may possess a conformation substantially different than the native protein. In this case, it may be necessary to denature and reduce the protein and then to cause the protein to re-fold into the preferred conformation.

To determine which circularly permuted polypeptides or fusion proteins are preferred, the proteins should be assayed for biological activity. Such assays, well known to those of skilled in the art, generally fall into two categories; those that measure the binding affinity of the protein to a particular target, and those that measure the biological activity of the protein. Also structural evaluations are made.

The fusion proteins of the present invention are useful for a variety of applications such as separations, drug delivery, targeting, and in diagnostic assays. For example, an avidin fusion protein can be bound to a biotinylated substrate. The biological activity of the secondary molecule can then be used, for example, to capture and separate a particular molecule out of an impure solution. The purified molecule is then dissociated from the fusion protein. The lower biotin affinity of the fusion protein as compared to that of wild type avidin allows release of the fusion protein from the substrate and reuse of the fusion protein. The two binding pockets in the dcAvd may be of different kind but are the same two in each dcAvd. The dual-chain pseudo-tetrameric avidin containing two of these dcAvds has thus two plus two of these binding pockets. The two strong specificity of the fusion protein can be used similarly in other applications.

Besides of biotin, dcAvidin or scAvd could be engineered to bind some different ligands with half of the binding sites. Furthermore this dual-ligand protein platform could be modified by the means of site directed mutagenesis, molecular pharming or random mutagenesis to bind two different ligands regardless of biotin.

The amino acid in the binding site and close to binding site can be modified in order to change the biotin binding characteristics. Furthermore, these amino acid residues could be modified in order to improve the binding of some other molecule, or ligand, for example 2-(4'hydroxyazobenzene)-benzoic acid (HABA). The HABA-binding affinity of the circularly permuted avidin can be different from the wild type avidin HABA-binding affinity.

Exemplary ligands comprise HABA and its derivatives, proteins, small molecules (MW 100-300 D). As a definition, "ligand" means a molecule capable of binding to dual-chain or single-chain avidin. More preferably, dcAvidin or scAvidin are modified or mutated in order to change the ligand binding characteristics.

"Ligand" includes also biotin variants or derivatives described in Green, N. M. (1975). "Avidin." Adv Prot Chem 29: 85-133 the contents of which is incorporated herein by reference in its entirety. HABA variants and derivatives are described in Weber, P. C., M. W. Pantoliano, et al. (1994). "Structure-Based Design of Synthetic Azobenzene Ligands for Streptavidin." J. Am. Chem. Soc. 116: 2717-2724 the contents of which is incorporated herein by reference in its entirety.

The amino acids should be selected among the group of known biotin-binding residues, which are mentioned by Livnah et al. in Proc. Natl., Acad. Sci. USA 90, (1993) 5076-5080. For example, S16, Y33, T35, S75 and N118 can be mutagenised for these purposes.

The binding of the ligand can also be adjusted by changing amino acid residues not directly contacting the ligand. These residues should be selected such that they form contacts with the ligand-contacting residues. Examples of this kind of residues are N13 (which forms hydrogen bond with N118, which forms hydrogen bond to biotin in avidin), M18 (which lines the residue Y33, which forms hydrogen bond to biotin in avidin). Furthermore, even modification in residues far away from binding site could be used for binding adjusting.

The modification could be performed by using standard site-specific mutagenesis. Targeted random mutagenesis and selection procedures could be also employed for this purpose.

Further, the amino acid residues in the protein surface could be modified in order to get chemically reactive groups available. These groups could then be used to attach different types of molecules to the dcAvd/scAvd.

The amino acids selected for this purpose can be taken close to ligand-binding site, in order to bring the attached molecule close to the bound ligand. In this situation, the ligand could be used to bring another molecule close to the protein-attached molecule by attaching the other selected molecule to the ligand.

The possible attachment sites close to ligand binding site are amino acid residues, but not restricted to, N42, E74, N104, R114.

The attachment site could be also selected so that it brings the attached molecule long away from the ligand-binding site. For this purpose, residues K9, N24 and R26 could be used, for example.

The amino acid can be mutated to a residue having the selected chemical reactivity. In order to get highly specific targeting site in protein, a cysteine residue can be introduced replacing the original residue. Cysteine residue can be then used to tightly attach other molecules for example using maleimide chemicals for this purpose. Unnatural amino acids could also be used for this purpose (Anthony-Cahill, S. J., and Magliery, T. J. (2002) Curr Pharm Biotechnol 3, 299-315), when expressed in suitable host, being engineered to perform this task.

It could be possible to modify the protein surface so that a new non-covalent binding site for some other molecule appears. The binding site could be also adjustable by properties of the protein environment (pH, temperature), which makes the binding adjustable (Ingham et al., (2004) J Biol Chem 279, 28132-28135).

The modification could be performed by using standard site-specific mutagenesis. Targeted random mutagenesis and selection procedures could be also employed for this purpose.

The attached molecule can be, but not restricted to, synthetic molecule, like fluorophore; protein, like enzyme; chelating agent; like radioactive material binding molecule. The dcAvd/scAvd can be also attached to a surface of a carrier material via the reactive group. The carrier could be a microparticle, for example.

The attachment of a molecule to the surface of a protein allows one to use this kind of construction for applications, where fluorescence energy resonance transfer (FRET) could occur between a fluorophore linked with protein and a fluorophore linked to ligand. Analogously, enzymes locating close to each other in the protein surface and attached to the ligand could allow enhanced performance due to high local concentration and good spatial arrangement, achieved for example by using two different ligand binding dcAvd variant and corresponding ligand-coupled enzymes coupled with different ligands each.

Dual chain avidin (dcAvd) can also be used as a fusion-partner. Due to the design of the molecule one fusion protein, dcAvd, contains two binding sites (in contrast to only one as would be the case with wild-type avidin) and upon "pseudo-tetramer" formation the functional quaternary structure can be attained as a result of dimerization of the dcAvd and not tetramerization as would be the case with wild-type avidin.

The constructed dual chain avidin (dcAvd) provides a structural scaffold for avidins with mixed affinity properties. Therefore its variants have enormous value in applications. This rationale derives from the fact that the dual-chain avidin is a genetically fused entity, which enables the engineering of the avidin subunit properties separately. It is possible to maintain the high affinity towards biotin by two of the binding sites while modifying the affinity in other two sites as desired. One preferred embodiment is to change two of the binding sites reversible which enables mild detachment of bound materials by free biotin (Laitinen, O. H. et al. FEBS Lett 461, 52-8 (1999), Laitinen, O. H. et al. Biochem J 363, 609-17 (2002), Qureshi, M. & Wong, S. Protein Expr. Purif. 25, 409 (2002), Qureshi, M. H. et al. J Biol Chem 2, 2 (2001)). Still another preferred embodiment is to modify half of the binding sites so that it is possible to attach to their close proximity such smart polymer conjugates that are able to respond to changes in pH, light intensity and temperature (Ding, Z. et al. Nature 411, 59-62 (2001), Shimoboji, T. et al. Bioconjug Chem 12, 314-9 (2001)) and thereafter alter the binding characteristic of the modified sites by adjusting these physical/chemical parameters.

The dual-affinity avidins of the present invention can be utilised in numerous different bioseparation techniques. For example, these molecules might allow the dcAvd mutant to be firmly immobilised on a biotin-functionalised surface or on a carrier material by the high-affinity native binding sites while enabling use of the modified free binding sites with selected affinity for the catch and release of biotin-coupled molecules. Likewise, the avidins of the present invention might find use in nanotechnology, e.g. in generation of more sophisticated structures and materials. The two high-affinity binding sites may be used for attachment of the protein via biotin to other building blocks in the molecular setting, and the rapidly reversible sites could be used as dynamic binding sites controlled, for example, by the concentration of free ligands. The dynamic binding site could function as a switch between two states controlled by the conditions used in the system.

In single-chain avidin (scAvd), where two dcAvd-molecules are fused together via a linker to form a single polypeptide with four binding sites for biotin, each of the four binding sites can be modified by protein engineering independently. Therefore, it is possible to have even four different binding sites in one polypeptide, all of which are also located identically in the quaternary structures of these proteins. This allows construction of divergent protein tools, in which ligand binding properties, ligand specifities and/or, for example, loop displayed peptides and other modifications can be positioned exactly as desired. Exemplary ligands binding to single-chain avidin comprise proteins, small molecules, modified biotins, HABA etc.

As a fusion partner scAvd provides completely new possibilities, because the four binding sites in one polypeptide constitute the whole quaternary structure, there is no need for scAvd containing fusion protein to form oligomeric assemblies, providing that the other fusion partner is also monovalent. Owing to this property, scAvd can be fused easily to multi-valent-proteins and even membrane proteins like receptors.

In order to bring new types of functions to dcAvd/scAvd scaffold, other proteins could be used as building blocks.

The idea could be to move a part of another protein to dc/scAvd. This could be done by moving only a limited region (for example one loop) from protein to protein (Pazy et al., (2003) J. Biol. Chem. 278, 7131-7134). The selected region can be selected by comparing the 3D structures or sequence alignments of proteins.

Furthermore, whole subunit could be moved from another protein. Preferably, structurally similar proteins having similar subunit-interface regions could be used for this purpose. For example, avidin related proteins or streptavidin could be used.

By using this rationale, more functions could be obtained. For example, a protein having different type of ligand affinity could be combined. The combined protein may be modified by circular permutation to bring the C/N termini to proper orientation allowing the linking to cpAvd to form dcAvd or scAvd.

By adjusting the linker between dcAvds, the oligomeric state of the final form could be adjusted. By using a linker shorter than 12 amino acid residues (0-8 for example), one may be able to prevent the formation of pseudotetrameric molecule, but rather dimeric avidin with eight binding sites is obtained. This rationale has been previously used when diabodies are created (Holliger et al., (1993) Proc. Natl. Acad. Sci. USA 90, 6444-6448).

The present invention is further described by the following non-limiting examples.

EXAMPLE 1

Planning of the Constructs

The 3D structure of avidin tetramer was examined in aim to find those β-strands of the barrels where the polypeptide transition from one subunit to the other would create as little steric disturbance as possible. The study revealed that in the quaternary structure, β-strand 4 in one subunit and strand 6 in another subunit of the structural dimer are juxtaposed. Moreover, when β-strand 4 goes up in one barrel, the β-strand 6 goes down in the neighbouring subunit. Therefore the loops 4→5 and 5→6 of the neighbouring subunits were used as a monomer-monomer transition point in the planned fused dual-chain avidin, dcAvd (SEQ ID NO:2), (FIGS. 1A and B). The determination of the transition point consequently pre-destined the places of the termini of the circularly permuted avidins to be as following: N-terminus of the first circularly permuted avidin monomer (cpAvd5→4) is located before the β-strand 5 in the wild-type sequence and the new C-terminus followed the β-strand 4. Correspondingly, the second circularly permuted avidin monomer (cpAvd6→5) started just before the α-strand 6 and ended after the β-strand 5.

In the circularly permuted avidin monomers, cpAvd5→4 and cpAvd6→5, the original N- and C-termini were fused with an artificial linker composed of a hexapeptide GGSGGS (SEQ ID NO:3). Both constructs started with the normal signal sequence of avidin followed by the three first N-terminal amino acid residues of native avidin to ensure the correct cleavage by signal peptidase. However, other signal sequences could be used and the three first N-terminal amino acid residues of native avidin could be left out. Finally, the dual-chain avidin was produced by fusing together the two circularly permuted avidin monomers described above (FIGS. 1A and B). A tripeptide spacer SGG was used to connect the C terminus of cpAvd5→4 to the N terminus of cpAvd6→5 and the resultant dual chain fusion was designated as dcAvd.

DNA Constructs and Recombinant Baculoviruses

In the first step in generation of the circularly permuted avidin monomers the signal sequence of avidin plus the two first amino acids of avidin were PCR amplified from avidin cDNA with forward primer AK33 (5'-CTGCTAGATCTATG-GTGCACGCAACCTCCCC-3') (SEQ ID NO:4) and reverse primer Sig-2 (5'-cctggc agagaggccggga-3') (SEQ ID NO:5) the product was digested with BglII and ligated into BamHI and StuI treated pFASTBAC1 plasmid (Bac-To-Bac™, Gibco BRL, Life Technologies, Gaithersburg, Md., USA).

In the next step in the case of cpAvd5→4 the region between beta strands 5 and 8 was PCR amplified with forward primer 54N1 5'-aag agg acc cag ccc acc tt-3' (SEQ ID NO:6) (coding also for the third amino acid, K, of avidin) and reverse primer 54C1 5'-gga gcc tcc gga gcc tcc ctc ctt ctg tgt gcg cag-3' (SEQ ID NO:7) (which inserts also the GGSGGS (SEQ ID NO: 3) linker after the beta strand eight). At the same time in a different tube the region between the beta strands 1 and 4 was PCR amplified with forward primer 54N2 5'-gga ggc tcc gga ggc tcc gcc aga aag tgc tcg ctg-3' (SEQ ID NO:8) (which codes also for the GGSGGS (SEQ ID NO: 3) linker, and the sequence is identical with the GGSGGS (SEQ ID NO: 3) coding part present in 54C1) and reverse primer 54C2 5'-tgggc aagct tca ctt gtt gat ggt gtt ttg-3' (SEQ ID NO:9) (which contains a stop codon and a HindIII restriction site). These two PCR products were purified and used as a template in the subsequent PCR step, in which the fragments containing complementary regions (the GGSGGS (SEQ ID NO: 3) region) were combined and amplified with the terminal primers (54N1 and 54C2). This product was treated with HindIII and ligated into StuI and HindIII treated pFASTBAC1 derivative containing the signal sequence and the first two amino acids.

Similarly in the case of cpAvd6→5 the region between beta strands 6 and 8 was PCR amplified with forward primer 65N1 5'-aag tcc acc act gtc ttc acg-3' (SEQ ID NO:10) (which adds also the third amino acid, K, of avidin) and reverse primer 54C1, as previously described, (which inserts also the GGSGGS (SEQ ID NO: 3) linker after the beta strand eight). In a different tube the region between beta strands 1 and 5 was PCR amplified with forward primer 54N2, as previously described, (which codes also for the GGSGGS (SEQ ID NO: 3) linker, and the sequence is identical with the GGSGGS (SEQ ID NO: 3) coding part present in 54C1) and reverse primer 65C2 5'-agaca aagct tca ctc tga aaa ctt cca att g-3' (SEQ ID NO:11) (which contains a stop codon and a HindIII restriction site). These two PCR products were purified and used as a template in the subsequent PCR step, in which the fragments containing complementary regions (the GGSGGS (SEQ ID NO: 3) region) were combined and PCR amplified with the terminal primers (65N1 and 65C2). This product was treated with HindIII and ligated into StuI and HindIII treated pFASTBAC1 derivative containing the signal sequence and the first two amino acids.

The dcAvd was constructed using the two above described constructs (cpAvd5→4 and cpAvd6→5) as templates. In the first step cpAvd5→4 was PCR amplified with forward primer AK33, described above, and reverse primer dual1 5'-gtggtg-gatccgccggacttgttgatggtgttttgtgt-3' (SEQ ID NO:12) (which codes also for the SGG monomer to monomer linker and contains a BamHI restriction site. This product was digested with BglII and BamHI and ligated into BamHI treated pFASTBAC1 and named pFASTBAC1(cpAvd5→4(no-stop)). In the next step cpAvd6→5 was PCR amplified with forward primer dual2 5'-ccggcggatccaccactgtcttcacgggc-3' (SEQ ID NO:13) (which also codes for the SGG linker and contains a BamHI restriction site) and reverse primer 65C2, as described above, (which contains a stop codon and a HindIII restriction site). This product was digested with BamHI and HindIII and ligated into previously obtained pFASTBAC1 derivative containing cpAvd5→4 and the spacer SGG, which was also treated with BamHI and HindIII.

EXAMPLE 2

Production and Purification of the Mutant Avidins

The circularly permuted avidin monomers and the dual-chain avidin were produced in baculovirus infected insect cells (Bac-To-Bac™, Gibco BRL, Life Technologies, Gaithersburg, Md., USA) and they were purified from the cell extracts by 2-iminobiotin-agarose affinity chromatography essentially as described in detail elsewhere (Laitinen, O. H. et al. *FEBS Lett* 461, 52-8 (1999), Airenne, K. J. et al. *Protein Expression and Purification* 9, 100-108 (1997)). In the baculovirus expression system the pFASBAC1 plasmid serves as a donor vector and the expression cassette, including the coding region for cpAvd5→4, cpAvd6→5 and dcAvd can be transferred from it using site specific transposition into recombinant baculovirus genomes (according to the manufacturers instructions). These recombinant genomes were used in transfections of the insect cells, in which the primary recombinant baculovirus stocks were generated. These stocks were used in consequent insect cell infections.

Briefly, the insect cell infections were carried out with cells that were transferred to a biotin-free medium. Infections were allowed to proceed for 72 hours, and after that the cells were collected by centrifugation (1500 g, 5 min). The cell pellet was dissolved into a lysis buffer (50 mM Tris-HCl, 2 mM EDTA, 150 mM NaCl, 1% Triton X-100, pH 8) and incubated on ice for 30 minutes. After that the cell extract was sonicated and centrifuged (15000 g 20 min) and the pH of the supernatant was adjusted to 11 with 5 M NaOH and NaCl was added to a final consentration of 1 M. Then the cell extract was applied to a 2-iminobiotin agarose column washed previously with binding buffer (50 mM Na-carbonate, 1 M NaCl). Bound proteins were eluted from the column with 50 mM Na-acetate, pH 4.

EXAMPLE 3

Biotin Binding Experiments

Reversibility of biotin binding and affinity towards 2-iminobiotin were determined with an IAsys optical biosensor (Affinity Sensors, Cambridge, UK) (Table 1.) as described in detail by Marttila et. al. (Marttila, A. T. et al. FEBS Lett 441, 313-7 (1998)). Briefly, The 2-iminobiotin ligand was immobilized onto the carboxymethyldextran surface of a cuvette using N-hydroxysuccinimide activation. Binding of various concentrations of avidin or avidin mutants onto 2-iminobiotinylated surface was measured in a 50 mM borate buffer (pH 9.5) containing 1 M NaCl at 20° C. The 2-iminobiotin cuvettes were regenerated with 20 mM HCl. The kinetic rate constants for association ($k_{ass}$) and dissociation ($k_{diss}$) were calculated using the Fast Fit program package (Affinity Sensors). The obtained rate constants were used to calculate $K_d$(rel) according to $K_d=k_{diss}/k_{ass}$. Equilibrium data obtained from measurements with different protein concentrations were used to calculate the dissociation constant Kd(eq).

TABLE 1

The association (kass) and dissociation (kdiss) rate constants and the affinity towards 2-iminobiotin for different avidins were determined with an IAsys optical biosensor. Kd(eq) was determined experimentally from the binding curves whereas the Kd(rel) was calculated from the rate constants. The reversibility value corresponds to reversibility from biotin surface.

| Protein | $k_{ass}$ (M$^{-1}$s$^{-1}$) | $k_{diss}$ (s$^{-1}$) | $K_d$(eq) (M) | $K_d$(rel) (M) | reversibility |
|---|---|---|---|---|---|
| wt Avd | $(5.5 \pm 0.5) \times 10^5$ | $(1.9 \pm 1.4) \times 10^{-3}$ | $(2.2 \pm 1.0) \times 10^{-8}$ | $(3.4 \pm 2.5) \times 10^{-8}$ | 9% |
| cpAvd5→4 | $(2.6 \pm 0.3) \times 10^5$ | $(1.6 \pm 0.7) \times 10^{-3}$ | $(1.5 \pm 0.5) \times 10^{-8}$ | $(5.9 \pm 2.6) \times 10^{-8}$ | 9% |
| cpAvd6→5 | $(3.9 \pm 1.2) \times 10^4$ | $(3.9 \pm 2.2) \times 10^{-3}$ | $(5.5 \pm 2.3) \times 10^{-7}$ | $(9.9 \pm 7.6) \times 10^{-7}$ | 16% |
| dcAvd | $(9.8 \pm 1.3) \times 10^4$ | $(1.1 \pm 0.5) \times 10^{-3}$ | $(4.1 \pm 1.2) \times 10^{-8}$ | $(1.1 \pm 0.5) \times 10^{-7}$ | 8% |

The reversibility of biotin binding was also measured using IAsys apparatus. In the reversibility assay, the sample proteins were allowed to bind to the biotinylated cuvette surface in PBS containing 1 M NaCl. After the equilibrium was reached, the cuvette was filled with PBS, 1 M NaCl containing biotin (423 μg/ml) and the dissociation of the proteins was monitored for one hour.

The colorimetric HABA-assay was performed essentially as described by Green (Green, N. *Methods in Enzymology* 18, 418-424 (1970)). Dual-chain avidin (dcAvd) in 100 mM phosphate buffer (pH 7) was saturated with excess HABA and the absorbance was measured at 500 nm with a Beckman DU640 spectrophotometer. After that, excess biotin, which replaces HABA from the binding site, was added to the sample and the absorbance at 500 nm was measured again. The observed change in the absorbance was used to calculate the number of free binding sites in dcAvd.

CpAvd5→4 showed similar biotin-binding characteristics as the wt avidin in both assays whereas the circularly permuted monomer cpAvd6→5 was more reversible and it exhibited reduced affinity as compared to the wt avidin. Interestingly, the dual chain avidin dcAvd showed similar reversibility as wt avidin and its affinity to 2-iminobiotin was decreased only negligibly. The number of biotin-binding sites per dual-chain avidin pseudo-tetramer (is actually a dimer with four binding sites) was determined in a colorimetric HABA-assay according to Green (Green, N. *Methods in Enzymology* 18, 418-424 (1970)). The average from two independent experiments gave an approximation of 3.3 free biotin-binding sites per dimeric molecule (pseudo-tetramer).

EXAMPLE 4

Structure Analyses

Quaternary status of the avidin mutants were determined by high performance liquid chromatography (HPLC), using a Superdex 200 HR 10/30 column (Amersham Pharmasia Biotech AB) connected to a Shimadzu HPLC system with SCL-10A VP system controller, RF-10A XL fluorescence detector and SPD-M10A VP diode array detector. The data obtained was processed with Class VP 5.03 program. As a running buffer we used 50 mM Na-phosphate, 650 mM NaCl, pH 7.2. All runs were performed with flow speed of 0.5 ml/min and the molecular weight markers were BSA (68 kDa), ovalbumin (43 kDa) and cytochrome c (12.4 kDa).

According to gel filtration chromatography performed in the absence of biotin the deduced molecular weights (Table 2) indicated that all constructs had folded correctly and formed quaternary structures like that of the wt avidin; two dual-chain avidins formed a pseudo-tetramer. In the denaturing SDS-PAGE both circularly permuted avidin monomers had apparent molecular weights corresponding to a wt monomeric form (FIG. 2), whereas dcAvd had a molecular weight of ≈32 kDa which corresponds well to its theoretical molecular weight. Moreover, we observed also that cpAvd6→5 was more heavily glycosylated than cpAvd5→4.

EXAMPLE 5

Stability Analyses

Thermal stability of the mutants was studied by using a SDS-PAGE-based method essentially as described in detail by Bayer et al. (Bayer, E. A. et al. *Electrophoresis* 17, 1319-1324 (1996)). Briefly, the protein sample in the absence or presence of biotin was diluted to a final concentration of 0.2 mg/mil in 50 mM Na-carbonate buffer, and the proteins were acetylated by adding acetyl NHS ester. Equal amount of SDS-PAGE sample buffer was added to each sample and the protein was incubated at different temperatures (between 25-100° C.) for 20 minutes. After that the samples were subjected to SDS-PAGE analysis and the gel was finally stained with Coomassie brilliant blue. Dissociation of the proteins into their subunits was observed from the gels and the transition temperatures, wherein half of the protein was (pseudo-)tetrameric and half monomeric were determined.

Proteinase K assay was performed essentially as described by Laitinen et al. (Laitinen, O. H. et al. *FEBS Lett* 461, 52-8 (1999)). Briefly, protein samples (50 µl, 1 mg/ml) with of without three times molar excess of biotin were diluted with equal volume of 100 mM Tris-HCl, pH7.8 and incubated in the presence of proteinase K (1:25 w/w) at 37° C. Samples were taken at designated time intervals and stored at −20° C. SDS-PAGE sample buffer was added to each sample before they were boiled and subjected to SDS-PAGE. The amount of intact avidin monomer present in the samples was determined from Coomassie brilliant blue stained gels.

Figure 3:
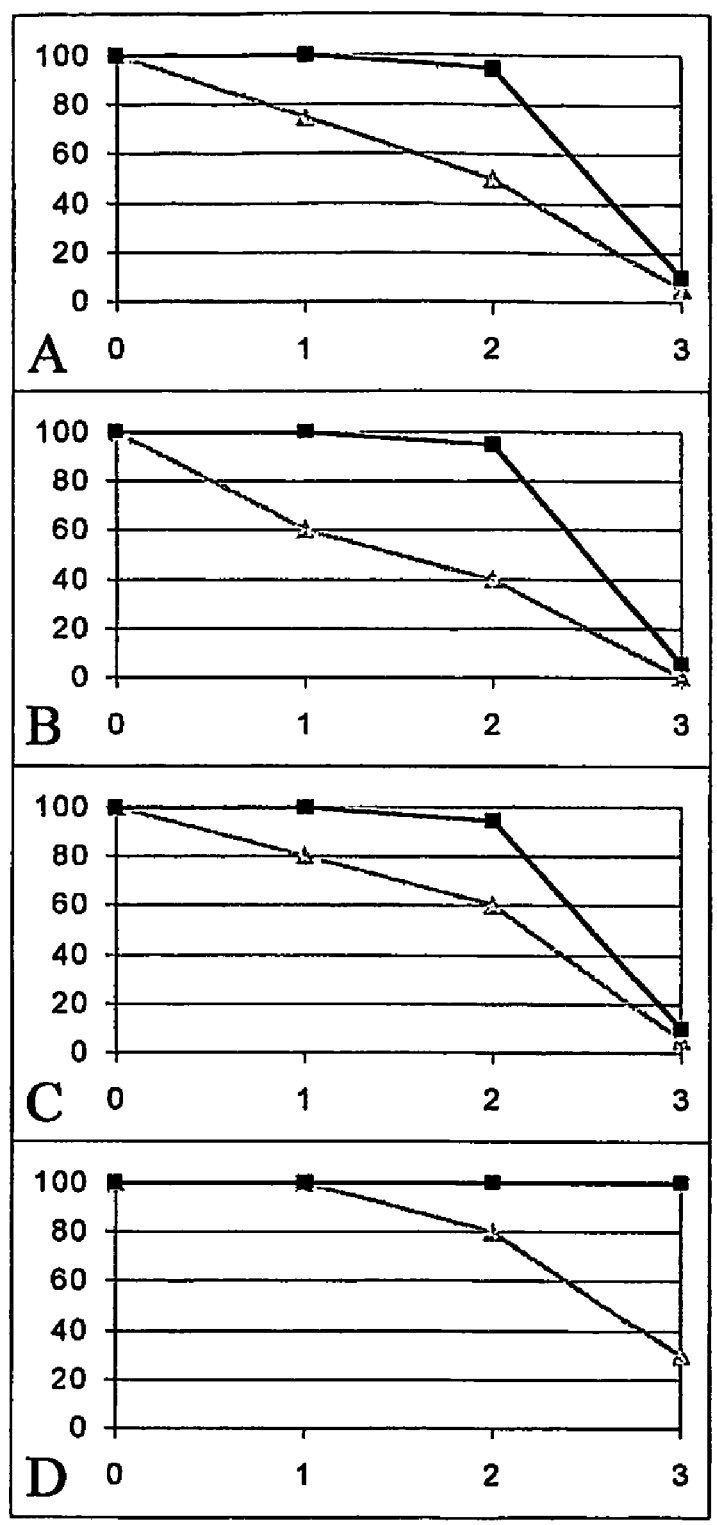
FIG. 3. Sensitivity of the mutants to proteinase K treatment. The values indicate the percentage of intact monomer present in the sample after 30 min (1) 60 min (2) and 16 hours (3) treatment. The samples are (A) cpAvd5→5, (3) cpAvd6→5, (C) dcAvd and (D) wt avidin.

The results are shown in Table 2 and revealed that the mutants were not quite as stable as the wt avidin. The durability of the mutants in the presence of proteinase K was also tested (FIG. 3) and all constructs were more prone for cleavage than wt avidin.

TABLE 2

The molecular weights (MW) were deduced form the gel filtration experiments. The stability parameters were obtained from heat/SDS-PAGE analysis. Transition temperature ($T_r$) is a temperature wherein half of the tetramer/pseudo-tetramer was broken into monomers in the presence (+btn) or absence of biotin.

| Protein | MW (kDa) | $T_r$ (° C.) | $T_r$ + btn (° C.) |
|---|---|---|---|
| wt Avd | 62 | 60 | 95 |
| cpAvd5→4 | 52 | 45 | 75 |
| cpAvd6→5 | 56 | 40 | 70 |
| dcAvd | 56 | 40 | 75 |

EXAMPLE 6

Production of a Mutated Dual-Chain Avidins (dcAvd)

Mutagenesis of CpAvd5→4 and CpAvd6→5

The numbering of the mutagenised amino acid residues in cpAvd molecules (Y33H, I117C, S16A, T35A) is according to mature chicken avidin amino acid residue numbering (SEQ ID NO: 1. The signal peptide is not included in numbered amino acid residues. 24 first amino acid residues of the sequence belong to signal sequence and are processed away during the posttranslational modification of the avidin).

Site-directed mutagenesis of the avidin cDNA, cpAvd6→5 or cpAvd5→4 was performed using the QuikChange (Stratagene, La Jolla, Calif., USA) or megaprimer (Sarkar, G. & Sommer, S. S. (1990) Biotechniques 8, 404-407.) mutagenesis methods. Mutagenised forms of cpAvd6→5 and cpAvd5→4 were then joined together to form the chimeric dcAvds by ligation after BamHI/HindIII digestion into a pFASTBAC1 donor vector. Details of the constructs are summarised in Table 3.

pFASTBAC1(cpAvd5-+4(no-stop))-plasmid was mutagenised by QuikChange method using oligonucleotides Q1 (5'-AGG GTC GGC TCG AAC ATC TT) (SEQ ID NO:14) and Q2 (5'-AAG ATG TTG CAG CCG ACC CT) (SEQ ID NO:15). The resulting plasmid was sequenced and named pFASTBAC1 (p54(I117C)).

pFASTBAC1-plasmid containing cDNA of cpAvd6→5 was mutagenised by QuikChange method using oligonucleotides Y33H.1 (5'-CAC AGG CAC CCA CAT CAC AGC CG) (SEQ ID NO:16) and Y33H.2 (5'-CGG CTG TGA TGT GGG TGC CTG TG) (SEQ ID NO:17). The resulting plasmid was sequenced and named pFASTBAC1 (p65(Y33H)). The mutations S16A and T35A were introduced by analogous way.

Figure 8:
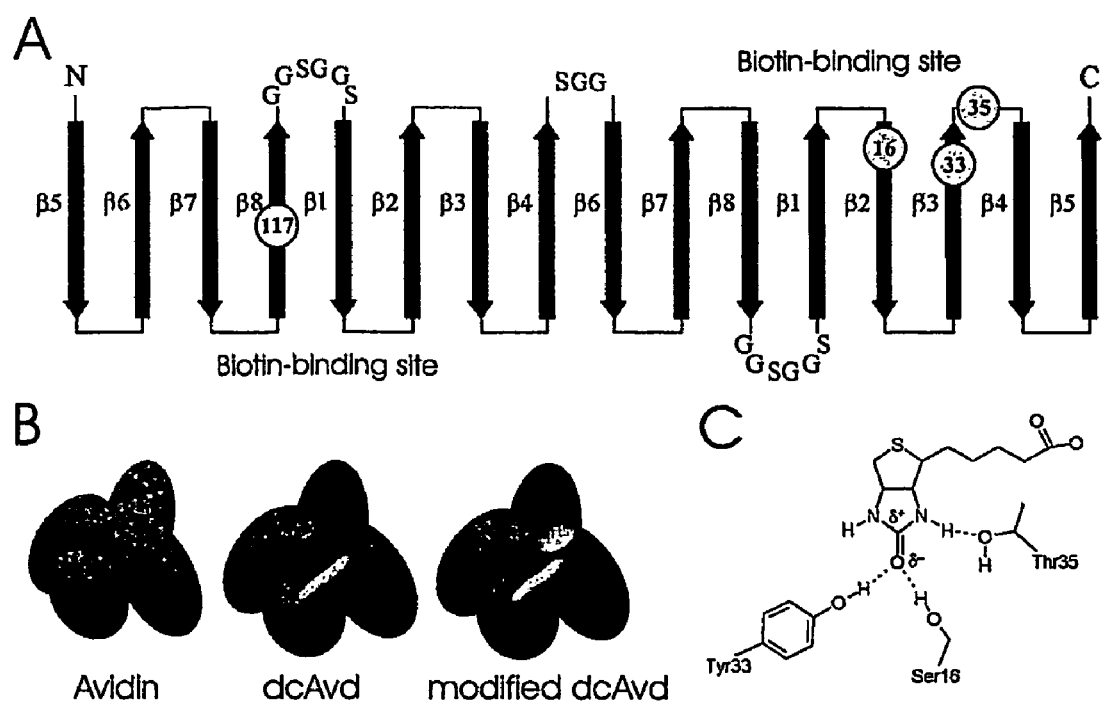
FIG. 8. (A) Representation of the topology of the secondary structure elements of dcAvd. The original circularly permuted monomers are coloured red and blue. The peptide linkers connecting the old C- and N-terminus of avidin in cpAvd5→4 (blue) and cpAvd6→5 (red) as well as the linker which connects the cpAvds to form dcAvd are shown in black and green letters, respectively. The locations of the mutagenised residues are shown by circles. The yellow circles refer to the modified biotin-binding residues. GGSGGS is disclosed as SEQ ID NO: 3. (B) Schematic representation of one possible quaternary structure of dcAvd and modified dcAvd. Colour codes as in (A). The peptide linker connecting the cpAvds is shown as a green tube. (C) Schematic representation of the biotin-binding residues mutagenised in this study and their interactions with biotin.

The topology of the secondary structure elements of the mutated dual-chain avidin (dcAvd) is presented in FIG. 8.

TABLE 3

Description of the dual chain avidin mutants.

| Protein | Mutation in cpAvd5→4 domain | Mutation in cpAvd6→5 domain | Description |
|---|---|---|---|
| dcAvd | none | none | Original dual chain avidin, fusion of the two circularly permuted avidins |
| dcAvd(I117C$_{5→4}$) | I117C | none | Stabilising disulphide bridge formation between the cpAvd5→4 domains of dcAvd |
| dcAvd (I117C$_{5→4}$S16A$_{6→5}$) | I117C | S16A | Mutation of a biotin-binding residue |
| dcAvd (I117C$_{5→4}$Y33H$_{6→5}$) | I117C | Y33H | Mutation of a biotin-binding residue |
| dcAvd (I117C$_{5→4}$T35A$_{6→5}$) | I117C | T35A | Mutation of a biotin-binding residue |

EXAMPLE 7

Cloning of pFASTBAC1(cp54(I117C)+cp65(Y33H))

Recombinant baculoviruses were generated using these vectors according to the Bac-To-Bac™ manufacturer's instructions (Gibco BRL, Life Technologies, Gaithersburg, Md., USA). Proteins were produced in baculovirus-infected Sf9 insect cells in biotin-free medium as previously reported (Laitinen et al., (2002) Biochem J 363, 609-617). The produced proteins were purified in a single step by affinity chromatography on 2-iminobiotin agarose column (Laitinen et al., (2001) J Biol Chem 276, 8219-8224).

The pFASTBAC1(cp65(Y33H)) was used as a template in PCR-reaction with primers dual2 and 65C2. The resulting product was extracted from 1% agarose gel, digested with BamHI/HindIII and ligated to pFASTBAC1 (cp54(I117C)) digested with BamHI and HindIII. The resulting plasmid was sequenced.

Expression of cp54(I117C)+cp65(Y33H) was carried using Bac-to-Bac expression system. 2-iminobiotin affinity chromatography was used to isolate the protein from infected insect cells.

EXAMPLE 8

Dissociation Analysis of Mutagenised Avidins

Figure 4:
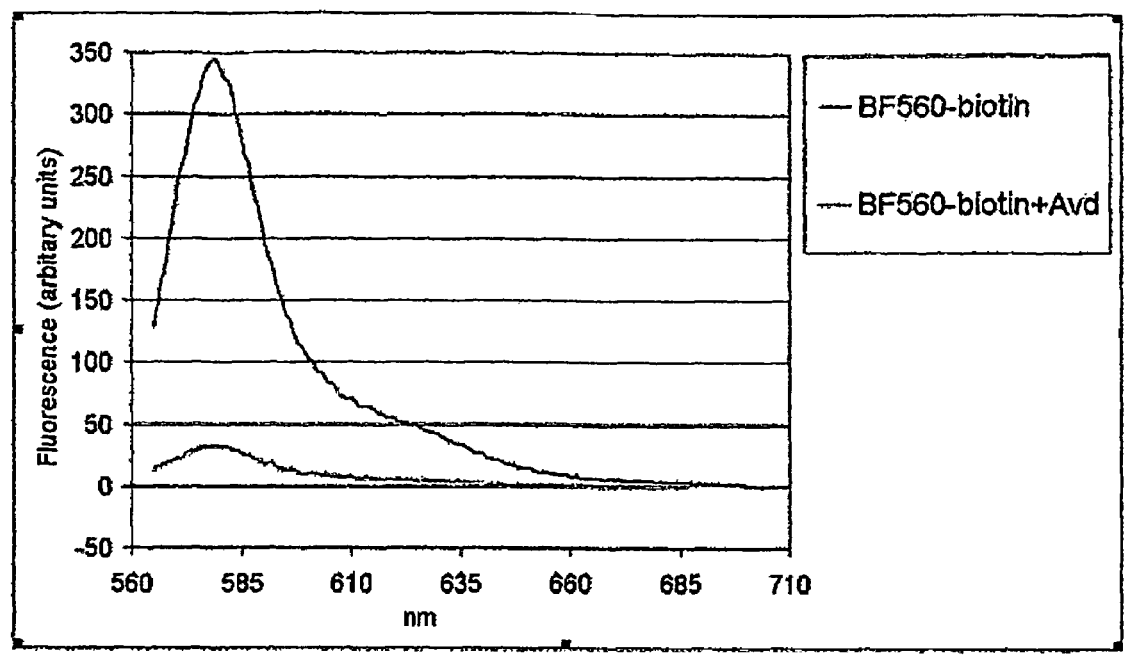
FIG. 4. The quenching of biotin-coupled BF560 by avidin. The spectra of 50 nM biotin-Bf560 solution in 50 mM Na-phosphate containing 650 mM NaCl was measured (red). Chicken avidin (Belovo S. A., Bastogne, Belgium) was added to final subunit concentration of 83 nM and green spectra was obtained.

The biotin-binding properties of produced mutagenised dcAvds were analysed by method based on the quenching of biotin-coupled fluorescent probe ArcDia BF560 (ArcDia Ltd., Turku, Finland) due to binding to avidin (FIG. 4). PerkinElmer LS55 luminometer was used for measurements. FIG. 4 shows the quenching of biotin-coupled BF560 by avidin. The spectra of 50 nM biotin-Bf560 solution in 50 mM Na-phosphate containing 650 mM NaCl was measured (red). Chicken avidin (Belovo S. A., Bastogne, Belgium) was added to final subunit concentration of 83 nM and green spectra was obtained.

Figure 5:
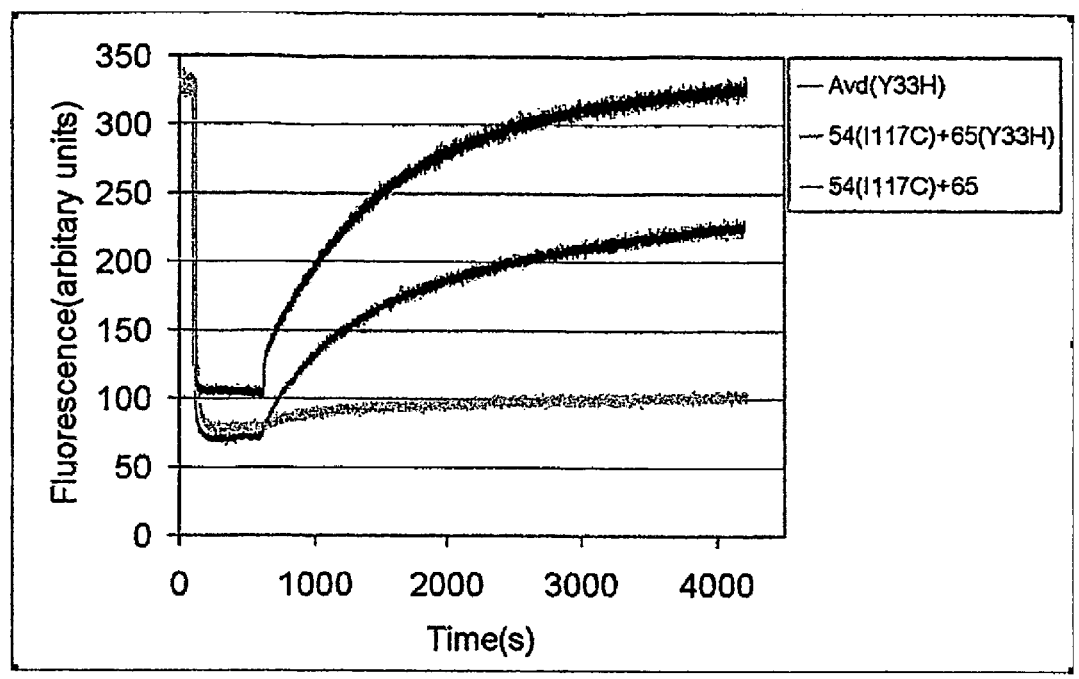
FIG. 5. The dissociation of biotin-coupled fluorescent probe (ArcDia BF560) with excess unlabeled biotin from proteins analyzed in this example. Avd(Y33H) (Marttila, A. T. et al. Biochem J. 369, 249-254 (2003)) shows rapid and complete dissociation of the fluorescent biotin probe from the four identically mutagenised (Y33H) subunits of tetramer (black). cp54(I117C)+cp65, instead, showed slow dissociation of the fluorescent biotin probe (green), comparable to that of wild-type avidin (not shown). Only half of the binding sites of cp54(I117C)+cp65(Y33H) have the mutation, and approximately half of the bound biotinylated probe is released within one hour (red).

Briefly, 50 nM free biotin-Bf560 solution in 50 mM Na-phosphate containing 650 mM NaCl was measured using excitation at 560 nm (2.5 nm slit) and emission was collected at 578 nm (5 nm slit). Continuous stirring (setting low) was used throughout the analysis. After 100 sec measurement, the protein under study was added to final biotin-binding subunit concentration 50 nM and the measurement was continued for 500 sec. After that, free biotin was added to final concentration of 5 μM and the signal was measured for 3600 sec at room temperature (23±0.5° C.) (FIG. 5). FIG. 5 shows the dissociation of biotin-coupled fluorescent probe (ArcDia BF560) with excess unlabeled biotin from proteins analyzed in this example. Avd(Y33H) (Marttila, A. T. et al. Biochem J. 369, 249-254 (2003)) shows rapid and complete dissociation of the fluorescent biotin probe from the four identically mutagenised (Y33H) subunits of tetramer (black). cp54(I117C)+cp65, instead, showed slow dissociation of the fluorescent biotin probe (green), comparable to that of wild-type avidin (not shown). Only half of the binding sites of cp54(I117C)+cp65(Y33H) have the mutation, and approximately half of the bound biotinylated probe is released within one hour (red).

Figure 9:
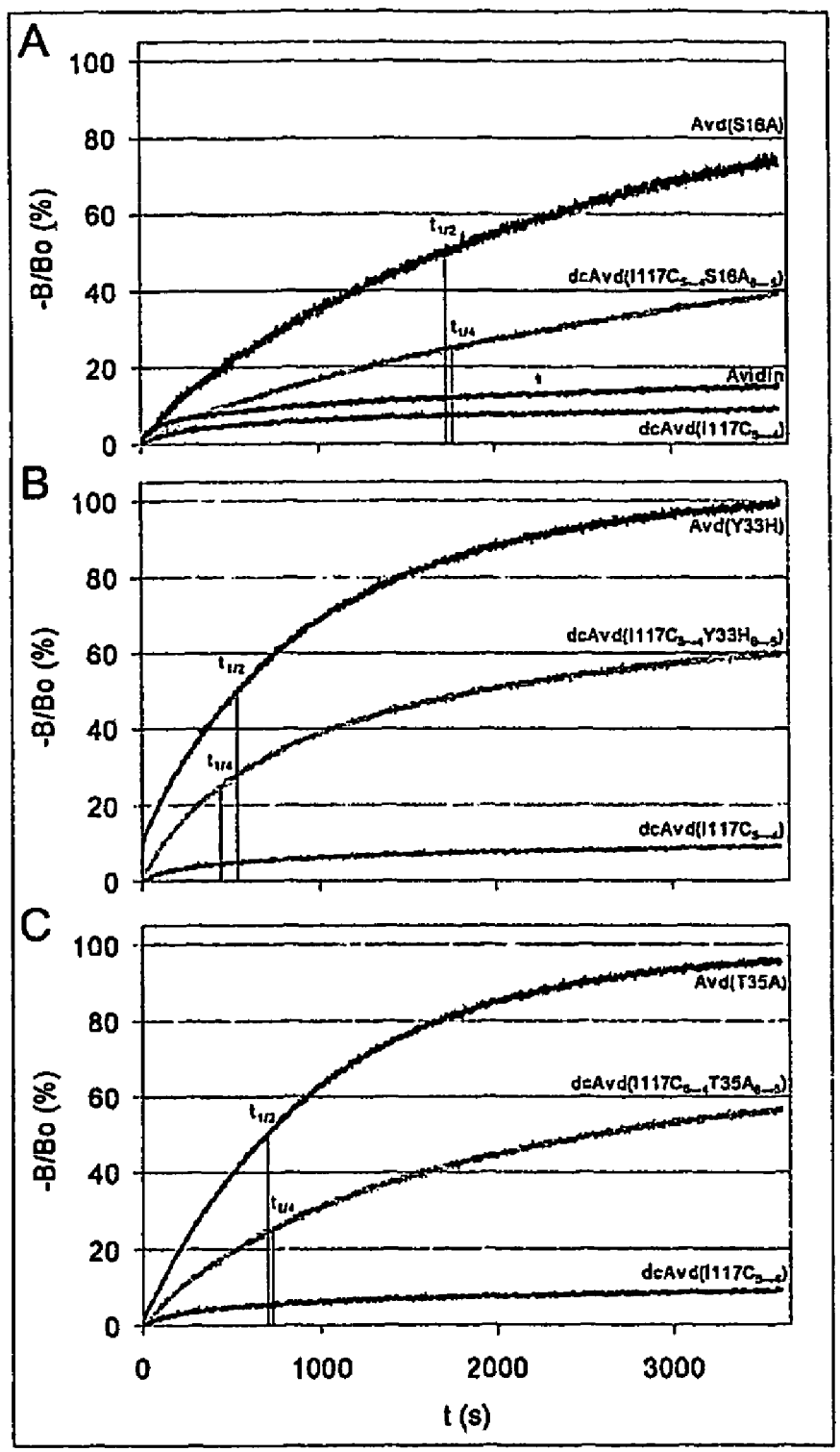
FIGS. 9(A-C) show the protein under study was allowed to bind BF560-biotin conjugate, which causes fluorescence quenching. After that, a 100-fold excess of free biotin was applied to the sample and the release of the fluorescent biotin was observed via the increase in the fluorescence signal. The time points determined for 25% release (t¼) of the fluorescent biotin conjugate for dcAvd samples and 50% release (t½) of conjugate for mutated avidins are indicated.

A one-phase dissociation model was used to analyse the data, as described elsewhere (Hytönen et al., (2004) Biochem J, in press). The dissociation rate constant (kdiss) was determined by fitting the equation −kdiss·t=ln(B/Bo) to the data. Bo is the measured maximum binding (100%) determined as the difference between the fluorescence of the free dye and the fluorescence of the protein-dye complex, and B is the amount of complex measured as a function of time. The first 500 seconds were omitted from the data to abolish the effect of the fast initial phase characteristic of avidin-BF560-biotin interaction (FIG. 9). The fraction of fluorescent biotin released after one-hour was determined, as well as the times of half-maximal (t½) and quarter-maximal (t¼) release. For dual chain avidins with modified binding sites, it was hypothesized that 50% of the binding sites would behave like those of wt avidin (cpAvd5S4 binding site of dcAvd was not modified). The dissociation data measured for wt avidin divided by two was subtracted from the data measured for the modified dual chain avidins and the dissociation curve was fitted to the difference as above.

EXAMPLE 9

Fluorescent Biotin Assay

The biotin-binding properties of the new mixed-affinity dcAvd-proteins were also analysed by the fluorescent biotin assay. In this analysis, dcAvd showed tight avidin-like biotin-binding (Table 4). On the basis of the results, the introduction of a stabilizing disulphide bridge between subunits had no effect on the biotin binding, since dcAvd(I117C54) showed binding characteristics similar to those of dcAvd (Table 4). When mutagenesis was used to alter the biotin-binding residues in two selected binding sites of dcAvd, a significant effect was observed. In the case of Y33H and T35A-mutations, about half of the bound biotin was released during the one hour measurement (FIG. 9). The mutation S16A also caused a faster dissociation rate (FIG. 9, Table 4). Since only two out of the four binding sites in these pseudotetrameric avidins were modified, they seemed to behave as independent combinations of wt and mutagenised avidins (Table 4).

A two-independent-site model was generated to describe the biotin-binding properties of the modified dual chain molecules, in which half of the binding sites behave as determined experimentally for unmodified binding sites (wt avidin) and half were considered as modified sites. The data measured for wt avidin was therefore divided by two and then subtracted from the measured dissociation data of the modified dcAvd-molecules to give the apparent behaviour of the two mutagenised binding sites in the pseudotetramer. The dissociation rate values obtained by this model were close to those measured for analogous avidin mutants (Table 4). To validate our model, we also compared the values determined directly from the data for t½ and t¼. The values of t½ obtained for the avidin mutants were fairly similar to the t¼ values obtained for dcAvd-proteins containing the analogous mutations in half of the binding sites (Table 4, FIG. 9) as expected on the basis of the model. In other words, the t¼ values obtained for dcAvd mutagenised at one of its two sites give the t½ values for the fast releasing sites when wt sites are excluded from the analysis by subtraction.

TABLE 4

Dissociation assay with fluorescent biotin conjugate. Dissociation of BF560-biotin conjugate from the proteins was measured at 23 ± 1° C. by a luminescence spectrometer. Release of the fluorescent biotin conjugate competed with 100-fold molar excess of free biotin.

| Protein | Release 1 h (%) | $t_{1/4}(s)^a$ | $t_{1/2}(s)^a$ | $k_{diss}(s^{-1})$ |
|---|---|---|---|---|
| Avidin | 14.1 | $ND^b$ | ND | $2.3 \times 10^{-5}$ |
| Avd(S16A) | 74.5 | 621 | 1728 | $3.6 \times 10^{-4}$ |
| Avd(Y33H) | 99.2 | 149 | 530 | $1.1 \times 10^{-3}$ |
| Avd(T35A) | 95.8 | 270 | 693 | $8.6 \times 10^{-4}$ |
| cpAvd5→4 | 20.6 | ND | ND | $3.4 \times 10^{-5}$ |
| cpAvd6→5 | 25.3 | 3557 | ND | $3.9 \times 10^{-5}$ |
| dcAvd | 10.1 | ND | ND | $1.4 \times 10^{-5}$ |
| dcAvd(I117C$_{5\to4}$) | 9.1 | ND | ND | $1.3 \times 10^{-5}$ |

TABLE 4-continued

Dissociation assay with fluorescent biotin conjugate. Dissociation of BF560-biotin conjugate from the proteins was measured at 23 ± 1° C. by a luminescence spectrometer. Release of the fluorescent biotin conjugate competed with 100-fold molar excess of free biotin.

| Protein | Release 1 h (%) | $t_{1/4}(s)^a$ | $t_{1/2}(s)^a$ | $k_{diss}(s^{-1})$ |
|---|---|---|---|---|
| dcAvd(I117C$_{5\to4}$S16A$_{6\to5}$) | 39.1 | 1762 | ND | $2.8 \times 10^{-4c}$ |
| dcAvd(I117C$_{5\to4}$Y33H$_{6\to5}$) | 59.9 | 435 | 1918 | $1.2 \times 10^{-3c}$ |
| dcAvd(I117C$_{5\to4}$T35A$_{6\to5}$) | 56.9 | 723 | 2585 | $7.8 \times 10^{-4c}$ |

[a]The time point of 25% and 50% release was determined directly from the measured data.
[b]Not applicable in the case of a one hour measurement.
[c]Dissociation rate for mutated binding site after subtraction of wt data.

EXAMPLE 10

Stability of the Proteins

The thermal stability of the mutant avidins was studied using DSC (Table 5). Both Avd(T35A) and Avd(S16A) unfolded at temperatures similar to wt avidin whereas Avd(Y33H) showed lower stability. CpAvd5→4 and cpAvd6→5 showed lower melting temperatures than wt avidin. However, dcAvd showed almost identical thermal stability to that of wt avidin. With the addition of biotin (3:1 ratio; biotin:binding site) the Tm was shifted to a clearly higher temperature in all proteins.

An increase in Tm was observed when mutation I117C was applied to dcAvd (Table 5). When mutations S16A and T35A were applied to dcAvd(I117C5→4), only relatively small changes in Tm, similar to those in wt avidin, were observed. The addition of the Y33H mutation, however, caused a more significant decrease in the Tm of dcAvd(I117C5→4).

The SDS-PAGE stability assay (39) gave results similar to DSC (Table 5). Mutations S16A and T35A did not have a significant effect on the stability of avidins. Mutation Y33H, however, radically destabilized the avidin in this assay. The introduction of mutation I117C5 4 to dcAvd stabilized the protein in a manner similar to that previously described for wt avidin (Nordlund et al., (2003) J Biol Chem 278, 2479-2483).

TABLE 5

Stability of the proteins. Transition midpoint temperatures of the oligomeric disassembly measured by an SDS-PAGE-based method. Heat-induced unfolding of the proteins determined by DSC. Apparent molecular weight obtained by gel filtration analysis.

| Protein | SDS-PAGE stability assay | | DSC | | | Gel filtration MW (kDa) |
|---|---|---|---|---|---|---|
| | $T_r/°C.$ (−)biotin | $T_r/°C.$ (+)biotin | $T_m(°C.)$ (−)biotin | $T_m(°C.)$ (+)biotin | $\Delta T_m^a$ (°C.) | |
| Avidin | 60 | 95 | 83.5 ± 0.1 | 117.0 ± 0.7 | 33.5 | 58.4 |
| Avd(S16A) | 55 | 80 | 84.3 ± 0.3 | 114.6 ± 0.2 | 30.3 | 55.9 |
| Avd(Y33H) | $ND^b$ | 75 | 73.0 | 106.3 | 33.3 | 51.0 |
| Avd(T35A) | 55 | 80 | 82.6 ± 0.1 | 113.2 ± 0.1 | 30.6 | 55.3 |
| cpAvd5→4 | 45 | 75 | 72.7 ± 0.4 | 111.3 ± 1.1 | 38.6 | 45.9 |
| cpAvd6→5 | 40 | 70 | 65.6 ± 0.7 | 102.0 | 36.4 | 48.0 |
| dcAvd | 40 | 75 | 80.2 ± 0.0 | 115.9 | 35.7 | 40.7 |
| dcAvd(I117C$_{5\to4}$) | 60 | 85 | 87.7 ± 0.1 | 118 | 30.3 | 43.0 |
| dcAvd(I117C$_{5\to4}$S16A$_{6\to5}$) | 60 | 80 | 87.7 | 112.9 | 25.2 | 51.3 |
| dcAvd(I117C$_{5\to4}$Y33H$_{6\to5}$) | $ND^b$ | 65 | 81.6 | 106.2 | 24.6 | 53.4 |
| dcAvd(I117C$_{5\to4}$T35A$_{6\to5}$) | 60 | 75 | 89.6 | 113.0 | 23.4 | 55.3 |

[a]$\Delta T_m$ is the change in $T_m$ upon addition of a three-fold molar excess of biotin.
[b]>50% of protein appears in the monomeric form in SDS-PAGE already at room temperature.

All of the produced dcAvd proteins with their affinity-decreasing mutations showed the desired properties. The binding sites containing mutations T35A and Y33H released biotin within one hour, whereas the unmodified binding sites had binding ability resembling that of wt avidin. Similar but milder behaviour was also observed with dcAvd containing mutation S16A. The changes in biotin-binding properties are also reflected in the thermal stability in the presence of biotin. The denaturation midpoint temperature (Tm) of holoprotein is lower in the case of modified dcAvds as compared to that of dcAvd with unmodified binding sites (Table 3). Altogether, the dcAvd forms were found to have high thermal stability even after mutagenesis of biotin-binding residues. These results suggest that even more radical manipulation could be performed on half of the binding sites in dcAvd without disturbing the high affinity biotin binding in the wt-like binding sites, such as mutagenesis of the residue W110 or multiple simultaneous mutations.

EXAMPLE 11

Construction of Expression Vector of Single-Chain Avidin (scAvd)

In this example two dcAvd-molecules are fused together tail-to-head via 12 amino-acid linker (GGSGSGSGSGSG) (SEQ ID NO: 31) to form a polypeptide with four binding sites for biotin. Other forms of linker may be also used.

The pFASTBAC1-plasmid containing dual-chain avidin (dcAvd) sequence was mutagenized using QuikChange method with primers poisto1 (5'-GGC GGA TCT ACC ACT GTC) (SEQ ID NO:18) and poisto2 (5'-GAC AGT GGT AGA TCC GCC) (SEQ ID NO:19) in order to destroy the BamHI restriction site in the sequence. The obtained plasmid was sequenced and named pFASTBAC1 (p54+p65-poisto).

pFASTBAC1 (cp6→5) was used as a template in PCR reaction with primers Single2.2 (5'-CCG GCA GAT CTA CCA CTG TCT TCA CGG GC) (SEQ ID NO:20) and Malooppi65.4 (5'-ATC CTC GGA TCC CGA TCC GGA ACC TCC CTC TGA AAA CTT C) (SEQ ID NO:21). The primer Single2.2 includes a BglII site. The primer Malooppi65.4 extends the sequence of cpAvd6-5 at the C-terminus with sequence GGSGSGS (SEQ ID NO: 32) and includes a BamHI site. The obtained PCR-product was extracted from 1% agarose gel, digested with BamHI and BglII and cloned to BamHI-digested pFASTBAC1 (cpAvd5→4(no-stop))-plasmid. The obtained plasmid was sequenced and named pFASTBAC1(p54+p65looppi).

pFASTBAC1 (p54+p65-poisto) was used as a template in PCR reaction with primers MAlooppi54 (5'-GGC TCT GGT GGC TGG ATC CGG CTC TGG CAG CGG CAG GAC CCA GCC C) (SEQ ID NO:22) and A414 (5'-CTA CAA ATG TGG TAT GGC TG) (SEQ ID NO:23). The primer Malooppi54 extends the sequence of cpAvd5-4 at the N-terminus with sequence GSGSGSG (SEQ ID NO: 33) and includes a BamHI site. The obtained PCR-product was extracted from 1% agarose gel and cloned to pGEM-T-easy vector using TA-cloning method. The obtained plasmid was sequenced and named pGemTeasy(p54looppi+p65).

The pGemTeasy(p54looppi+p65) was digested with BamHI/HindIII, the obtained DNA-fragment was extracted from 1% agarose gel and cloned to BamHI/HindIII-digested pFASTBAC1(p54+p65looppi). The resulting plasmid was named pFASTBAC 1 (scAvd).

The polypeptide sequence of avidin is provided (SEQ ID NO:24).

EXAMPLE 12

Protein Production and Purification of Single-Chain Avidin (scAvd)

Recombinant baculoviruses encoding scAvd in *Spodoptera frugiperda* Sf9 insect cells were generated using this donor vector according to the Bac-To-Bac™ manufacturer's instructions (Gibco BRL, Life Technologies, Gaithersburg, Md., USA). Proteins were produced in baculovirus-infected Sf9 insect cells in biotin-free medium as previously reported (Laitinen et al., (2002) Biochem. J. 363, 609-617). The scAvd was purified in a single step by affinity chromatography on 2-iminobiotin agarose column, as previously described (Laitinen et al., (2001) J. Biol. Chem. 276, 8219-8224).

The produced scAvd was efficiently purified by 2-iminobiotin affinity chromatography which indicated that the produced protein was soluble and biologically active in the sense of ligand binding.

Figure 10:
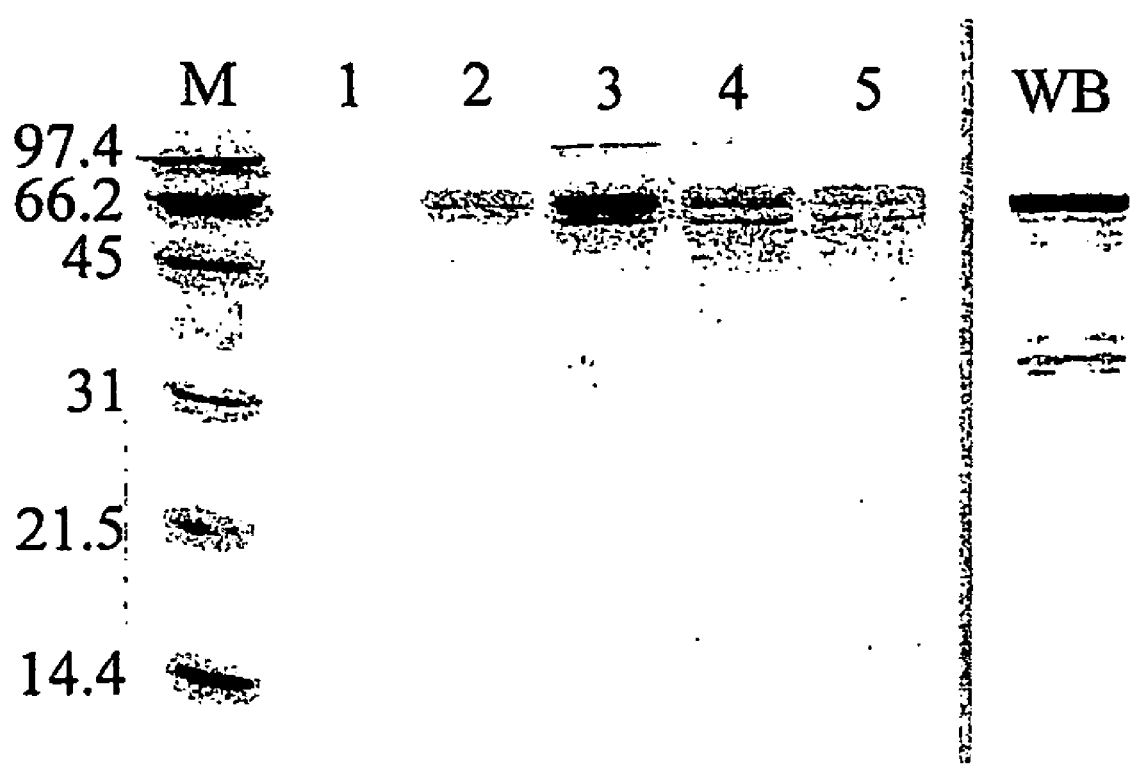
FIG. 10. Purification of scAvd. Coomassie-stained SDS-PAGE analysis of elution fractions 1-5 after 2-iminobiotin purification. Molecular weight standard (Bio-Rad Low weight) is indicated by "M". Western blot analysis with polyclonal anti-avidin is shown labelled "WB".

In the FPLC gel filtration analysis, scAvd eluted at the same volume as wt avidin indicating similar molecular size and physicochemical appearance in solution (Table 6). Purified scAvd existed in SDS-PAGE analysis in about 65 kDa form. The two close forms of the band are caused by the glycosylation of the protein. Only traces of about 30 kDa forms were detected, indicating the homogeneity of the purified protein (FIG. 10). Western blot analysis with polyclonal anti-avidin recognised the identical bands seen in Coomassie staining.

Dissociation assay with ArcDia™ BF560 fluorescent biotin (Hytönen et al., (2004) Biochem. J.) showed similar properties for avidins. Both dcAvd and scAvd showed slightly slower dissociation rate and lower total release at 25° C. In the measurement made at 50° C., all proteins exhibited rather similar characteristics. Measured dissociation rate constant and total release after one hour competition is shown in Table 6.

TABLE 6

Structural properties of avidins. FPLC gel filtration elution times and calculated molecular weights of the proteins. Measured number of free biotin-binding sites per quaternary unit. Quenching of the intrinsic fluorescence at 350 nm due to binding of biotin. Dissociation of fluorescent biotin conjugate from the proteins at 25° C. and 50° C.

| | Gel filtration | | Determination of free biotin-binding sites | | Dissociation of fluorescent biotin | | | |
|---|---|---|---|---|---|---|---|---|
| | | | | | 25° C. | | 50° C. | |
| | Elution time (min) | Molecular mass (kDa) | Number of sites | Fluorescence quenching (350 nm) (%) | $k_{diss}$ $(s^{-1})$ | Release 1 h (%) | $k_{diss}$ $(s^{-1})$ | Release 1 h (%) |
| Avidin | 31.5 | 58.4 | 3.34 | 47.7 | $2.3 \times 10^{-5}$ | 14.1 | $2.4 \times 10^{-4}$ | 71.5 |
| dcAvd | 32.9 | 40.7 | 3.86 | 51.4 | $1.5 \times 10^{-5}$ | 10.1 | $2.7 \times 10^{-4}$ | 67.4 |
| scAvd | 31.8 | 54.0 | 3.20 | 44.4 | $1.3 \times 10^{-5}$ | 8.8 | $2.5 \times 10^{-4}$ | 62.3 |

EXAMPLE 13

Radiobiotin Dissociation Assay

Figure 11:
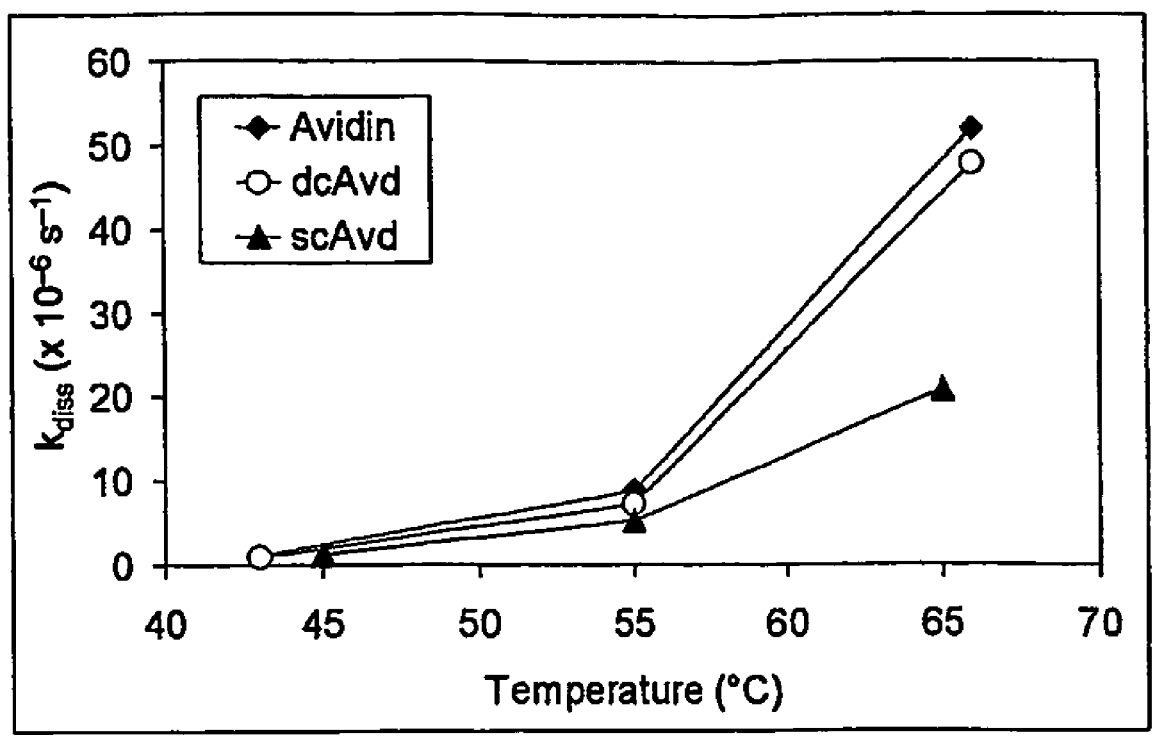
FIG. 11. Radiobiotin dissociation assay for scAvd. Temperature-dependence of biotin dissociation rates measured by the [3H]biotin dissociation assay. Dissociation rate constant of radiobiotin was determined at various temperatures. The dissociation rate constants determined previously for avidin and streptavidin are also shown. The determined kdiss-values are connected by lines.

Radiobiotin assay was performed for scAvd in various temperatures. Like avidin and dcAvd, scAvd exhibited extremely slow dissociation of [3H]biotin. Notably, the measured dissociation rate constants for scAvd were somewhat lower when compared to those of Avd and dcAvd. The dissociation rate constants determined from measured data are shown in FIG. 11.

EXAMPLE 14

Determination of Free Biotin Binding Sites of scAvd

The number of free binding sites was determined based on the quenching of the intrinsic fluorescence of avidin due to binding of biotin (Laitinen et al., (2003) J. Biol. Chem. 278, 4010-4014). The protein sample under study diluted to 2 ml volume in 50 mM NaPO4 pH 7.0+650 mM NaCl was titrated with 1 µl additions of 70 µM biotin solution in the same buffer. The protein concentration in this assay was 500±15 nM, and the concentration was determined by comparing the emission intensity averaged over 340-350 nm (excitation at 280 nm) to avidin standard sample. The protein sample was continuously mixed by magnetic stirrer.

Figure 12:
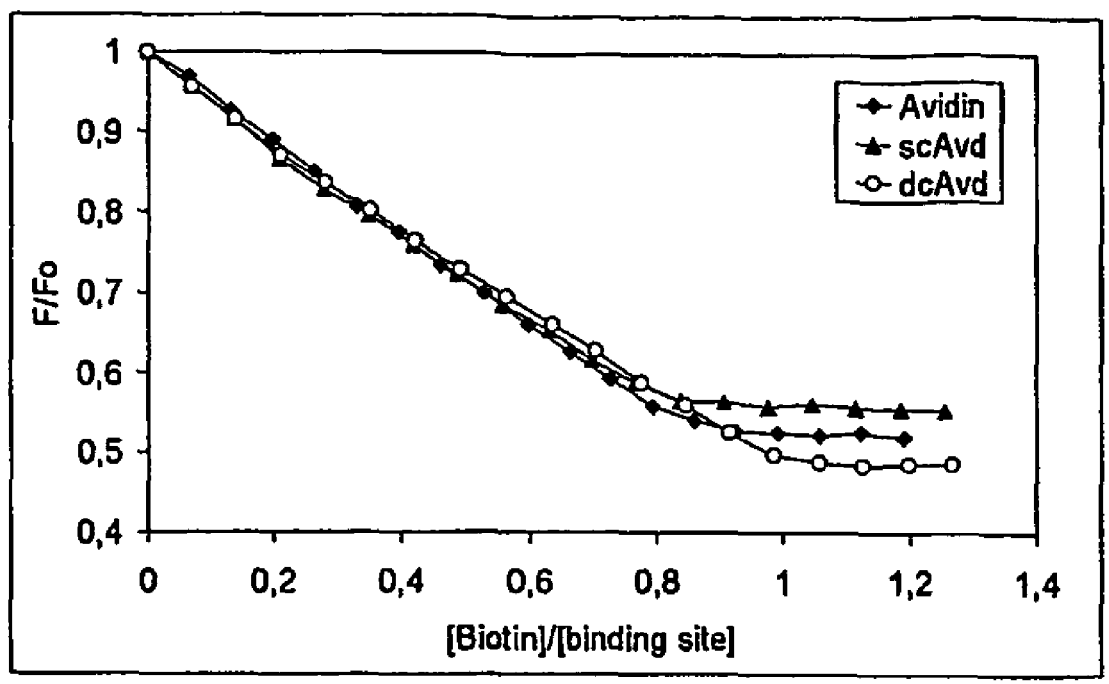
FIG. 12. Quenching of the intrinsic fluorescence by biotin binding. Protein sample was titrated by d-biotin and the emission intensity was measured at 350 nm wavelength. The number of free biotin-binding sites in proteins was determined from the data.

In the assay, emission intensity at 350 nm (5 nm slit) was measured by exiting the sample with 280 nm wavelength (2.5 nm slit). Intensity from each biotin concentration was averaged over eight second measurement. The end-point of the quenching was determined by fitting a line to obtained data and determining the total quenching by averaging the last three measured intensities (FIG. 12, Table 6).

It was found that scAvd showed somewhat lower activity (3.2 binding sites per molecule) when compared to avidin (3.3 binding sites per tetramer). Similar difference was also detected in the total quenching determined since 44.4% of the emission intensity of scAvd at 350 nm was quenched due to addition of biotin compared to 47.7% measured for avidin (FIG. 12, Table 6). The quenching measured for whole emission spectrum (290-500 nm) for the proteins due to biotin binding was 44.9% for avidin, 39.7% for scAvd and 45.1% for dcAvd.

EXAMPLE 15

Stability of Avidin, dcAvd and scAvd Determined by Microplate Assay

Both scAvd and dcAvd showed fast inactivation in assay performed at 100° C. Avidin control, instead showed significantly slower response to the heat treatment (not shown).

Figure 13:
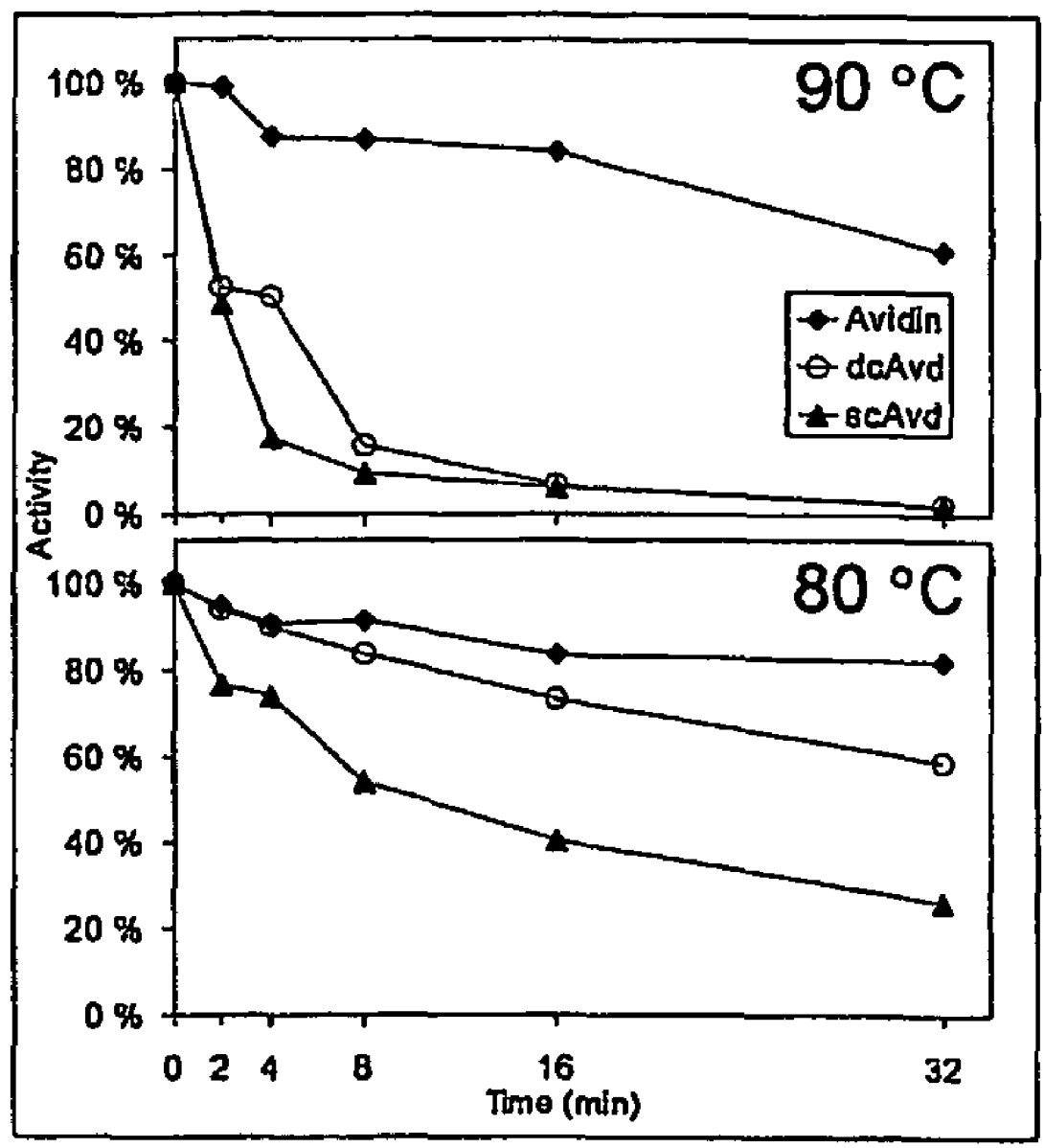
FIG. 13. Temperature sensitivity determined by microplate assay. The avidin, dcAvd and scAvd sample is treated with the indicated temperature for certain time and the ability to bind biotinylated alkaline phosphatase was determined by coating the microplate with the sample.
Figure 14:
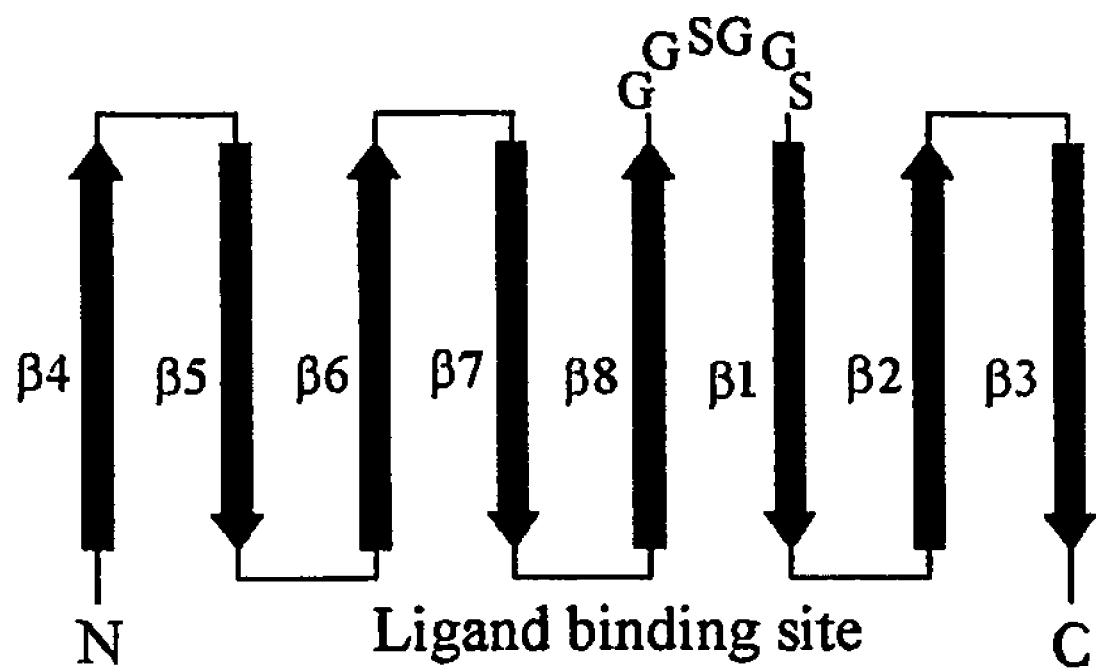
FIG. 14. Topology diagram of cpAvd4→3. GGSGGS is disclosed as SEQ ID NO: 3.
Figure 15:
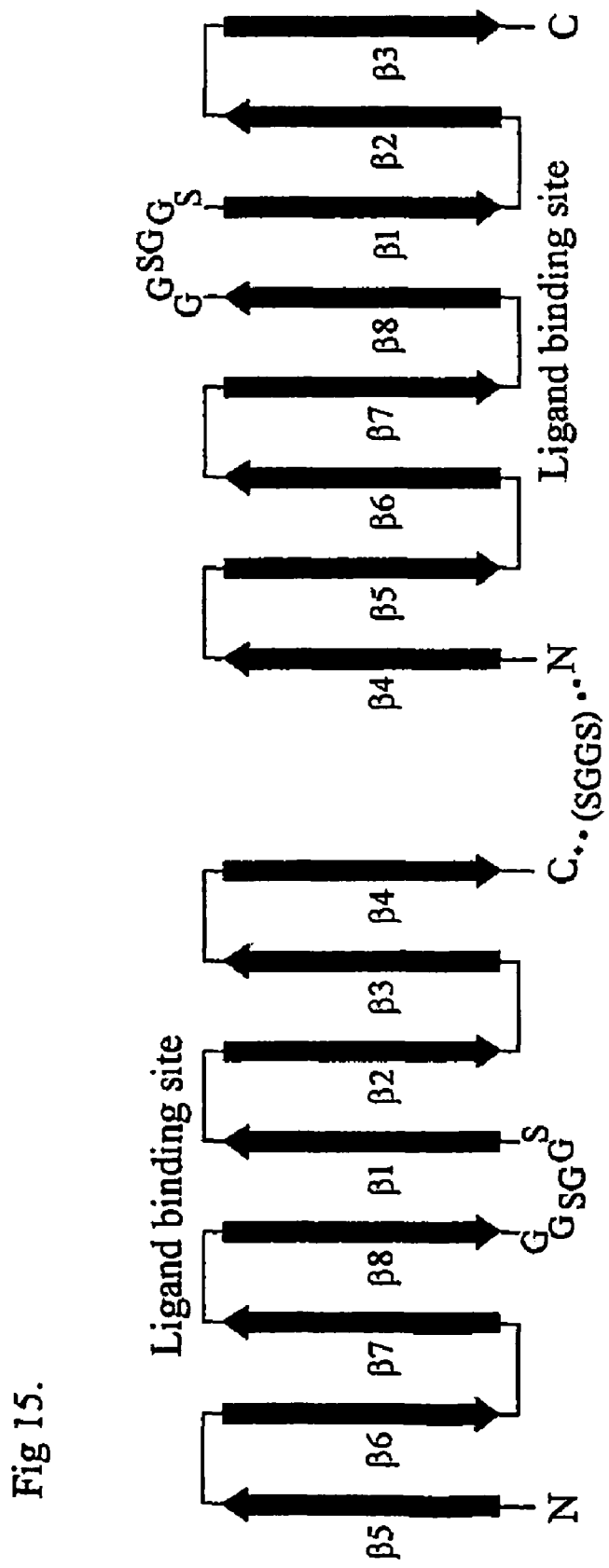
FIG. 15. The topology diagram of dual chain avidin dcAvd54+43. In the figure, the red part shows the circularly permuted avidin 5→4 and the blue part the circularly permuted avidin 4→3. GGSGGS & SGGS are disclosed as SEQ ID NOS 3 & 30, respectively.
Figure 16:
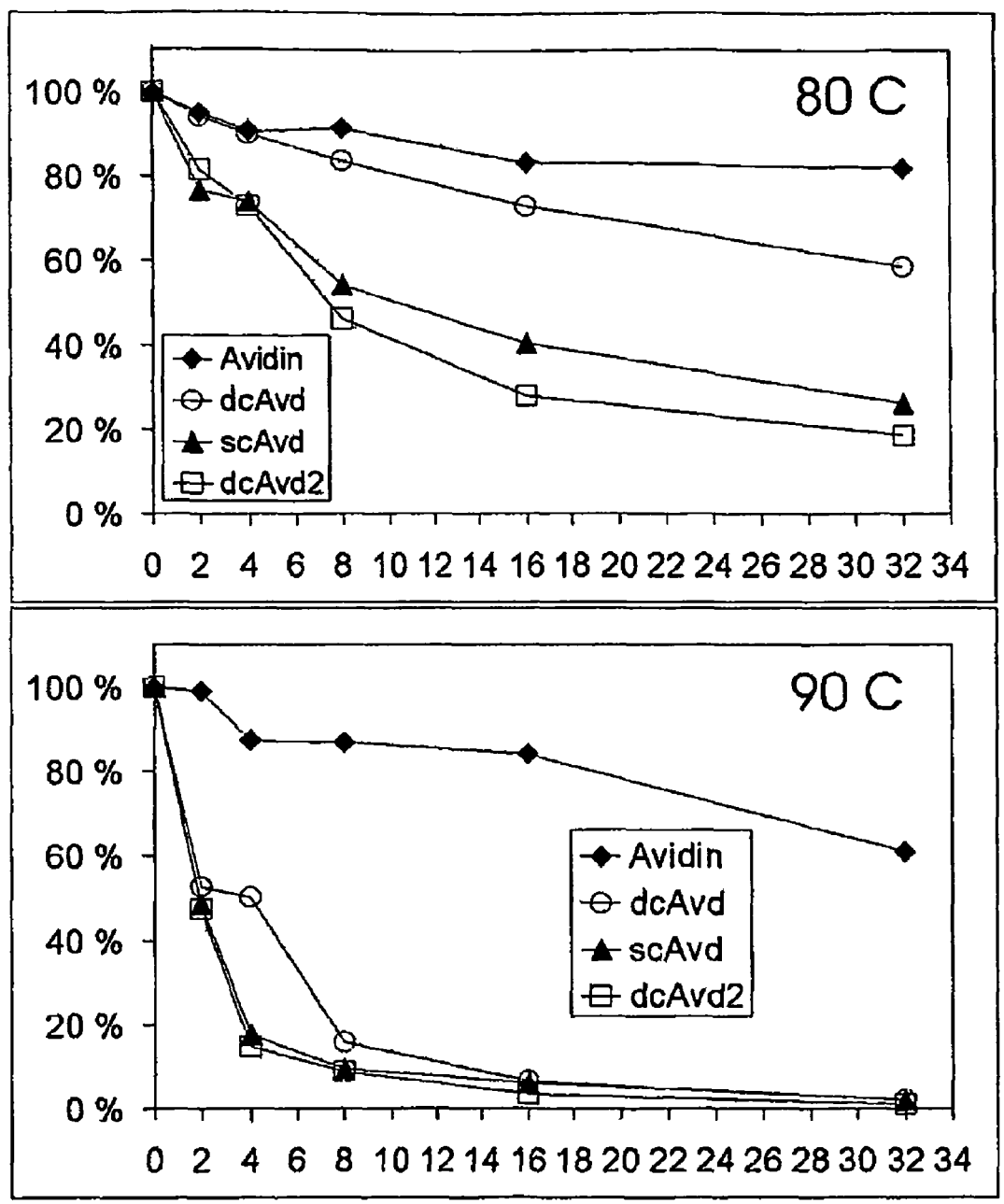
FIG. 16. Microplate stability assay. The assay is performed in two temperatures (80° C. and 90° C.) and the activity (y-axis) is measured after heat treatment for certain time period (x-axis). Dual chain avidin dcAvd54+43 is indicated by dcAvd2 in the figure.

When temperature was lowered to 90° C., scAvd and dcAvd still exhibited fast denaturation, dcAvd showing slightly higher activity at 4 min and 8 min time points. Avidin showed slow inactivation in this temperature and over 50% of the activity was present after 32 min treatment (FIG. 13).

At 80° C., all the proteins showed slow inactivation. The scAvd exhibited lowest temperature-resistance of the proteins. The activity of scAvd after 32 min treatment was 26% compared to those measured for avidin (82%) and dcAvd (59%) (FIG. 13).

EXAMPLE 16

Tuning of the Ligand Specificity and Affinity in Dual Chain Avidin and Avidin The aim is to find mutations leading to lower biotin binding affinity when compared to wt avidin (i.e. affinities $K_d \approx 10^{-3}$–$10^{-9}$ M and even lower).

To perform this, mutagenesis was targeted to the biotin-binding residues of avidin (Livnah et al., (1993) Proc Natl Acad Sci USA 90, 5076-5080). The 2-(4'hydroxyazobenzene)-benzoic acid (HABA) was selected as a target ligand (Livnah et al., (1993) Federation of European Biochemical Societies 328, 165-1682). This molecule is known to bind avidin with a mediocre affinity ($K_d \approx 6 \times 10^{-6}$ M) (Green, N. M. (1970) Methods Enzymol. 18, 418-424).

When serine 75 or asparagine 118 is mutated to another residue shown in Table 7, avidins with lower affinity-biotin are obtained. At the same time, the affinity to HABA is increased in the case of some mutations.

The mutagenesis of expression constructs was carried using standard methods. The proteins were produced by baculovirus expression system and isolated by affinity chromatography. The isolation of N118 mutants by affinity chromatography with 2-iminobiotin as an immobilised ligand was inefficient and therefore biotin affinity chromatography was used. Avidin mutants N118L and N118M were eluted with 0.1 M acetic acid indicating radically lowered binding affinity when compared to wt proteins. In comparison, we were not able to elute S75 mutants even by using 1.0 M acetic acid when biotin was used as the ligand in affinity chromatography.

The affinity to HABA was measured by fluorescence spectroscopy method. In this assay, avidin solution (50 nM) in Na—PO4 pH 7.0 containing 650 mM NaCl was titrated with small additions of HABA solution made in the same buffer. The avidin solution was excited by 280 nm light (slit 2.5 nm) and the emission at 350 nm (5 nm slit) was measured. The emission intensity was measured with several HABA concentrations. Binding curve $$F/F0 = a[HABA]/(Kd+[HABA])+c$$

was fitted to the obtained data. In this equation, F is the measured fluorescence in certain HABA concentration, F0 is the initial fluorescence and a and c are scaling factors. The results from the measurements are shown in Table 7.

TABLE 7

Binding of HABA to avidin and avidin mutants.

| Protein | $K_d$ (HABA) |
| --- | --- |
| Avd | $6.26 \times 10^{-6}$ |
| Avd(S75F) | $6.77 \times 10^{-6}$ |
| Avd(S75I) | $3.51 \times 10^{-6}$ |
| Avd(S75V) | $1.64 \times 10^{-6}$ |
| Avd(N118L) | $2.13 \times 10^{-6}$ |
| Avd(N118M) | $6.16 \times 10^{-7}$ |

In conclusion, by mutating N118 to methionine, we obtained around 10 times higher HABA affinity and significantly weakened biotin binding to mutated avidin. This difference is due to interactions lost between avidin and biotin and probably also due to better contact made between the methionine and HABA when compared to asparagine and HABA in the wt protein (Livnah et al., (1993) Proc Natl Acad Sci USA 90, 5076-5080; Livnah et al., (1993) Federation of European Biochemical Societies 328, 165-168).

In order to plant the best mutation N118M to dual chain avidin, the DNA encoding for 65 avidin was mutated using standard methods. The expression construct for bacterial expression was created as described in the article by Hytönen et al., (2004) Biochem. J., in press. In this method, the avidin signal peptide used in the expression of dual chain avidin in insect cells is replaced with a bacterial secretion signal peptide from ompA protein as described in the article by Hytönen et al., (2004) Biochem. J., in press. This method was also used to produce dual chain avidin.

The resultant protein DC 54+65(N118M) was isolated and purified by using 2-iminobiotin affinity chromatography. The resultant protein was analysed by the fluorescence spectroscopy method described above and the protein showed higher affinity to HABA when compared to wt avidin. Kd=2.21×10-6 M.

Since only half of the binding sites are modified in this protein, the resultant mutated dual chain avidin behaves as a combination of wt and mutated avidin, showing about three-fold higher affinity to HABA when compared to wt avidin.

By using the described strategy, also more mutations could be applied to dual chain avidin making it selectively binding some other ligand than biotin by two binding sites. The two binding sites could still bid biotin like wt protein. Analogously, same strategy could be applied to single chain avidin.

EXAMPLE 17

Production of Circularly Permuted Avidin CpAvd4→3 and its Fusion with CpAvd5→4 to Form Dual Chain Avidin dcAvd54+43

The circularly permuted avidin cpAvd4→3 was created by PCR method. First, a PCR reaction was carried out with primers 5,4N2 and cp34_C1 AATTTAAGCT TATGTTACGG CTGTGATGTA G (SEQ ID NO:27) using avidin cDNA as a template. The PCR product was extracted from agarose gel after electrophoretic analysis. The second PCR was carried out with primers 5,4C1 and cp34_C1 (AATTTAAGCT TATGTTACGG CTGTGATGTA G) (SEQ ID NO: 27). The PCR product was again extracted from agarose gel. PCR products from these reactions were combined in the third PCR reaction and they worked as megaprimers in this reaction.

The obtained DNA encoding for cpAvd4→3 was then cloned to a plasmid containing cp54 avidin (cpAvd5→4) and a SGGS (SEQ ID NO: 30) linker sequence. Restriction enzymes BamHI and HindIII were used in the cloning. The construct was confirmed by sequencing.

In cpAvd4→3, N- and C-terminus of avidin are joined by linker GGSGGS (SEQ ID NO: 3). Furthermore, part of the loop between beta strands 3 and 4 is removed, corresponding to residues 39ATSNEI44. In the circularly permuted avidin, the sequence starts before beta-strand 4 and ends after beta strand 3 (FIG. 14).

The obtained DNA was then joined to cpAvd5→4 to form dual chain avidin dcAvd54+43 (FIG. 15).

The resultant DNA was cloned to bacterial expression construct, wherein bacterial signal peptide from ompA protein is employed as described in the article by Hytönen et al., (2004) Biochem. J., in press. The protein is produced in *E. coli* and purified by using affinity chromatography with 2-iminobiotin as a target ligand as described in the article by Hytönen et al., (2004) Biochem. J., in press.

The resultant protein (dual chain avidin dcAvd54+43) was analysed by gel filtration chromatography as described in the article by Nordlund et al., (2004) J Biol Chem 279, 36715-9, and was found to form dimer in solution (pseudotetramer).

The biotin binding affinity was characterised by using fluorescent biotin dissociation assay as described above. The biotin conjugate was found to dissociate from the protein faster (kdiss=4.8×10−5 s−1) when compared to wt avidin (kdiss=2.3×10−5 s−1) indicating lower biotin binding affinity.

The stability of the protein was studied by microplate assay as described in the article by Nordlund et al., (2003) J Biol Chem 278, 2479-83. In this assay, 50 mM Na—PO4 buffer containing 100 mM NaCl was used and the protein was heated to 80° C. or 90° C. for certain time. After that, the capacity to bind fluorescent biotin was measured as described in the article by Nordlund et al., (2003) J Biol Chem 278, 2479-83. The results from this assay are shown in FIG. 16.

Dual chain avidin dcAvd54+43 amino acid sequence (SEQ ID NO:28) is presented in FIG. 17. The signal peptide is underlined as well as the peptide linkers between N- and C-terminus of circularly permuted avidins and the SGGS (SEQ ID NO: 30) linker connecting 5→4 and 4→3 avidins.

Dual chain avidin dcAvd54+43 DNA sequence (SEQ ID NO:29) is presented in FIG. 18

EXAMPLE 18

Structurally equivalent antiparallel eight β-strand (avidin fold) proteins could be modified by using the described methods. For example, but not restricted to, circularly permuted streptavidins could be produced analogously as the ones described above for avidin. Circularly permuted streptavidin can be made by joining the C- and N-terminus of the protein by a peptide linker (for example six amino acid residues) and introducing the new C/N-termini between β-strands 4 and 5. Similarly, the opening site can be between β-strands 3 and 4 or between β-strands 5 and 6. When these circularly permuted avidins are joined in one polypeptide chain by peptide linker (for example three or four amino acid residues), a dcStreptavidin can be obtained. When four circularly permuted streptavidins are joined in one polypeptide chain, or two dcStreptavidinds are fused, a scStreptavidin can be obtained. In the case of scStreptavidin, the dcStreptavidin units may be linked by 12 residue polypeptide, for example.

It is understood that the disclosed invention is not limited to the particular methodology, protocols, and reagents described as these may vary. It is also to be understood that the terminology used herein is for the purpose of describing particular embodiments only, and is not intended to limit the scope of the present invention, which will be limited only by the appended claims.

The invention claimed is:

1. A dual-chain avidin (dcAvd) comprising a fusion of two circularly permuted avidin monomers (cpAvd), the avidin monomers selected from the group consisting of:
   circularly permuted avidin monomer comprising a new N-terminus that is before β-strand 5 and a new C-terminus that is after β-strand 4 (cpAvd5→4);
   circularly permuted avidin monomer comprising a new N-terminus that is before β-strand 6 and a new C-terminus that is after β-strand 5 (cpAvd6→5); and
   circularly permuted avidin monomer comprising a new N-terminus that is before β-strand 4 and a new C-terminus that is after β-strand 3 (cpAvd4→3),
      wherein in the cpAvd, the original C-terminal amino acid and the original N-terminal amino acid are joined directly or via a linker, thus creating the new C-terminus and the new N-terminus, and the dual-chain avidin binds biotin or other ligand.

2. The dual-chain avidin of claim 1, wherein the avidin is selected from wild-type avidin, streptavidin, a variant of avidin, poultry avidin, and chicken avidin-related protein (AVR).

3. The dual-chain avidin of claim 1, wherein the original C-terminal amino acid and original N-terminal amino acid have been joined by a linker comprising one or more amino acids.

4. The dual-chain avidin of claim 3, wherein the linker is a hexapeptide comprising four glycine amino acids and two serine amino acids, and a glycine is connected to the C-terminal amino acid and a serine is connected to the N-terminal amino acid.

5. The dual-chain avidin of claim 1, wherein the circularly permuted avidin monomer has a biotin binding affinity that is different from the biotin-binding affinity of wild-type avidin.

6. The dual-chain avidin of claim 1, wherein the circularly permuted avidin monomer has a HABA-binding affinity that is different from the HABA-binding affinity of wild-type avidin.

7. The dual-chain avidin of claim 1, wherein the avidin monomer has been mutated by changing tyrosine 33 to histidine (Y33H), isoleucine 117 to cysteine (I117C), serine 16 to alanine (S16A), threonine to alanine (T35A), and/or asparagine 118 to methionine (N118M), as referenced by the mature chicken avidin amino acid residue numbering of SEQ ID NO:1.

8. The dual-chain avidin of claim 1, wherein the two circularly permuted avidin monomers are fused together directly or joined via a spacer.

9. The dual-chain avidin of claim 8, wherein the spacer is a peptide spacer of about 1 to 40 amino acids.

10. The dual-chain avidin of claim 9, wherein the spacer is a peptide SGG or SGGS (SEQ ID NO: 30).

11. A dual-chain pseudo-tetrameric avidin, comprising two dual-chain avidin molecules (dcAvd) of claim 1.

12. The dual-chain pseudo-tetrameric avidin of claim 11 that binds biotin.

13. A single-chain avidin (scAvd), comprising the two dcAvd molecules of the dual-chain pseudo-tetrameric avidin of claim 11 fused together to form a single polypeptide.

14. The single-chain avidin of claim 13, wherein the two dcAvd molecules are fused together via a linker.

15. The single-chain avidin of claim 14, wherein the linker is a 12 amino-acid linker GGSGSGSGSGSG (SEQ ID NO: 31).

16. An isolated polynucleotide encoding the dual-chain avidin of claim 1.

17. A recombinant vector comprising the polynucleotide of claim 16, wherein the polynucleotide is DNA.

18. A host cell comprising the polynucleotide of claim 16, wherein the polynucleotide is DNA.

19. A method for producing a dual-chain avidin (dcAvd) comprising expressing the dual-chain avidin in the host cell of claim 18, wherein the dcAvd is encoded by the polynucleotide.

* * * * *

SEQUENCE LISTING

```
<160> NUMBER OF SEQ ID NOS: 33

<210> SEQ ID NO 1
<211> LENGTH: 152
<212> TYPE: PRT
<213> ORGANISM: Gallus gallus
```

<400> SEQUENCE: 1

Met Val His Ala Thr Ser Pro Leu Leu Leu Leu Leu Leu Ser Leu
1               5                   10                  15

Ala Leu Val Ala Pro Gly Leu Ser Ala Arg Lys Cys Ser Leu Thr Gly
            20                  25                  30

Lys Trp Thr Asn Asp Leu Gly Ser Asn Met Thr Ile Gly Ala Val Asn
                35                  40                  45

Ser Arg Gly Glu Phe Thr Gly Thr Tyr Ile Thr Ala Val Thr Ala Thr
    50                  55                  60

Ser Asn Glu Ile Lys Glu Ser Pro Leu His Gly Thr Gln Asn Thr Ile
65                  70                  75                  80

Asn Lys Arg Thr Gln Pro Thr Phe Gly Phe Thr Val Asn Trp Lys Phe
                85                  90                  95

Ser Glu Ser Thr Thr Val Phe Thr Gly Gln Cys Phe Ile Asp Arg Asn
                100                 105                 110

Gly Lys Glu Val Leu Lys Thr Met Trp Leu Leu Arg Ser Ser Val Asn
            115                 120                 125

Asp Ile Gly Asp Asp Trp Lys Ala Thr Arg Val Gly Ile Asn Ile Phe
130                 135                 140

Thr Arg Leu Arg Thr Gln Lys Glu
145                 150

<210> SEQ ID NO 2
<211> LENGTH: 298
<212> TYPE: PRT
<213> ORGANISM: Gallus gallus

<400> SEQUENCE: 2

Met Val His Ala Thr Ser Pro Leu Leu Leu Leu Leu Leu Ser Leu
1               5                   10                  15

Ala Leu Val Ala Pro Gly Leu Ser Ala Arg Lys Arg Thr Gln Pro Thr
            20                  25                  30

Phe Gly Phe Thr Val Asn Trp Lys Phe Ser Glu Ser Thr Thr Val Phe
                35                  40                  45

Thr Gly Gln Cys Phe Ile Asp Arg Asn Gly Lys Glu Val Leu Lys Thr
    50                  55                  60

Met Trp Leu Leu Arg Ser Ser Val Asn Asp Ile Gly Asp Asp Trp Lys
65                  70                  75                  80

Ala Thr Arg Val Gly Ile Asn Ile Phe Thr Arg Leu Arg Thr Gln Lys
                85                  90                  95

Glu Gly Gly Ser Gly Gly Ser Ala Arg Lys Cys Ser Leu Thr Gly Lys
            100                 105                 110

Trp Thr Asn Asp Leu Gly Ser Asn Met Thr Ile Gly Ala Val Asn Ser
            115                 120                 125

Arg Gly Glu Phe Thr Gly Thr Tyr Ile Thr Ala Val Thr Ala Thr Ser
    130                 135                 140

Asn Glu Ile Lys Glu Ser Pro Leu His Gly Thr Gln Asn Thr Ile Asn
145                 150                 155                 160

Lys Ser Gly Gly Ser Thr Thr Val Phe Thr Gly Gln Cys Phe Ile Asp
                165                 170                 175

Arg Asn Gly Lys Glu Val Leu Lys Thr Met Trp Leu Leu Arg Ser Ser
            180                 185                 190

Val Asn Asp Ile Gly Asp Asp Trp Lys Ala Thr Arg Val Gly Ile Asn
            195                 200                 205

```
Ile Phe Thr Arg Leu Arg Thr Gln Lys Glu Gly Gly Ser Gly Gly Ser
    210                 215                 220

Ala Arg Lys Cys Ser Leu Thr Gly Lys Trp Thr Asn Asp Leu Gly Ser
225                 230                 235                 240

Asn Met Thr Ile Gly Ala Val Asn Ser Arg Gly Glu Phe Thr Gly Thr
                245                 250                 255

Tyr Ile Thr Ala Val Thr Ala Thr Ser Asn Glu Ile Lys Glu Ser Pro
            260                 265                 270

Leu His Gly Thr Gln Asn Thr Ile Asn Lys Arg Thr Gln Pro Thr Phe
        275                 280                 285

Gly Phe Thr Val Asn Trp Lys Phe Ser Glu
    290                 295

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide linker

<400> SEQUENCE: 3

Gly Gly Ser Gly Gly Ser
 1               5

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ctgctagatc tatggtgcac gcaacctccc c                              31

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cctggcagag aggccggga                                            19

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aagaggaccc agcccacctt                                           20

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 7
ggagcctccg gagcctccct ccttctgtgt gcgcag                                    36

<210> SEQ ID NO 8
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggaggctccg gaggctccgc cagaaagtgc tcgctg                                    36

<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tgggcaagct tcacttgttg atggtgtttt g                                         31

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aagtccacca ctgtcttcac g                                                    21

<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
agacaaagct tcactctgaa aacttccaat tg                                        32

<210> SEQ ID NO 12
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gtggtggatc cgccggactt gttgatggtg ttttgtgt                                  38

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
```

-continued

```
ccggcggatc caccactgtc ttcacgggc                                         29

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
agggtcggct cgaacatctt                                                   20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
aagatgttgc agccgaccct                                                   20

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
cacaggcacc cacatcacag ccg                                               23

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
cggctgtgat gtgggtgcct gtg                                               23

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggcggatcta ccactgtc                                                     18

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gacagtggta gatccgcc                                                     18
```

```
<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ccggcagatc taccactgtc ttcacgggc                                          29

<210> SEQ ID NO 21
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
atcctcggat cccgatccgg aacctccctc tgaaaacttc                              40

<210> SEQ ID NO 22
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ggctctggtg gctggatccg gctctggcag cggcaggacc cagccc                       46

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ctacaaatgt ggtatggctg                                                    20

<210> SEQ ID NO 24
<211> LENGTH: 581
<212> TYPE: PRT
<213> ORGANISM: Gallus gallus

<400> SEQUENCE: 24
```

Met Val His Ala Thr Ser Pro Leu Leu Leu Leu Leu Ser Leu
 1               5                  10                  15

Ala Leu Val Ala Pro Gly Leu Ser Ala Arg Lys Arg Thr Gln Pro Thr
                 20                  25                  30

Phe Gly Phe Thr Val Asn Trp Lys Phe Ser Glu Ser Thr Val Phe
            35                  40                  45

Thr Gly Gln Cys Phe Ile Asp Arg Asn Gly Lys Glu Val Leu Lys Thr
        50                  55                  60

Met Trp Leu Leu Arg Ser Ser Val Asn Asp Ile Gly Asp Asp Trp Lys
65                  70                  75                  80

Ala Thr Arg Val Gly Ile Asn Ile Phe Thr Arg Leu Arg Thr Gln Lys
                85                  90                  95

Glu Gly Gly Ser Gly Gly Ser Ala Arg Lys Cys Ser Leu Thr Gly Lys
            100                 105                 110

-continued

```
Trp Thr Asn Asp Leu Gly Ser Asn Met Thr Ile Gly Ala Val Asn Ser
            115                 120                 125
Arg Gly Glu Phe Thr Gly Thr Tyr Ile Thr Ala Val Thr Ala Thr Ser
        130                 135                 140
Asn Glu Ile Lys Glu Ser Pro Leu His Gly Gln Asn Thr Ile Asn
145                 150                 155                 160
Lys Ser Gly Gly Ser Thr Thr Val Phe Thr Gly Gln Cys Phe Ile Asp
                165                 170                 175
Arg Asn Gly Lys Glu Val Leu Lys Thr Met Trp Leu Arg Ser Ser
            180                 185                 190
Val Asn Asp Ile Gly Asp Asp Trp Lys Ala Thr Arg Val Gly Ile Asn
        195                 200                 205
Ile Phe Thr Arg Leu Arg Thr Gln Lys Glu Gly Ser Gly Gly Ser
        210                 215                 220
Ala Arg Lys Cys Ser Leu Thr Gly Lys Trp Thr Asn Asp Leu Gly Ser
225                 230                 235                 240
Asn Met Thr Ile Gly Ala Val Asn Ser Arg Gly Glu Phe Thr Gly Thr
                245                 250                 255
Tyr Ile Thr Ala Val Thr Ala Thr Ser Asn Glu Ile Lys Glu Ser Pro
            260                 265                 270
Leu His Gly Thr Gln Asn Thr Ile Asn Lys Arg Thr Gln Pro Thr Phe
        275                 280                 285
Gly Phe Thr Val Asn Trp Lys Phe Ser Glu Gly Gly Ser Gly Ser Gly
        290                 295                 300
Ser Gly Ser Gly Ser Gly Arg Thr Gln Pro Thr Phe Gly Phe Thr Val
305                 310                 315                 320
Asn Trp Lys Phe Ser Glu Ser Thr Thr Val Phe Thr Gly Gln Cys Phe
                325                 330                 335
Ile Asp Arg Asn Gly Lys Glu Val Leu Lys Thr Met Trp Leu Leu Arg
            340                 345                 350
Ser Ser Val Asn Asp Ile Gly Asp Asp Trp Lys Ala Thr Arg Val Gly
        355                 360                 365
Ile Asn Ile Phe Thr Arg Leu Arg Thr Gln Lys Glu Gly Gly Ser Gly
        370                 375                 380
Gly Ser Ala Arg Lys Cys Ser Leu Thr Gly Lys Trp Thr Asn Asp Leu
385                 390                 395                 400
Gly Ser Asn Met Thr Ile Gly Ala Val Asn Ser Arg Gly Glu Phe Thr
                405                 410                 415
Gly Thr Tyr Ile Thr Ala Val Thr Ala Thr Ser Asn Glu Ile Lys Glu
            420                 425                 430
Ser Pro Leu His Gly Thr Gln Asn Thr Ile Asn Lys Ser Gly Gly Ser
        435                 440                 445
Thr Thr Val Phe Thr Gly Gln Cys Phe Ile Asp Arg Asn Gly Lys Glu
        450                 455                 460
Val Leu Lys Thr Met Trp Leu Leu Arg Ser Ser Val Asn Asp Ile Gly
465                 470                 475                 480
Asp Asp Trp Lys Ala Thr Arg Val Gly Ile Asn Ile Phe Thr Arg Leu
                485                 490                 495
Arg Thr Gln Lys Glu Gly Ser Gly Gly Ser Ala Arg Lys Cys Ser
            500                 505                 510
Leu Thr Gly Lys Trp Thr Asn Asp Leu Gly Ser Asn Met Thr Ile Gly
        515                 520                 525
Ala Val Asn Ser Arg Gly Glu Phe Thr Gly Thr Tyr Ile Thr Ala Val
```

```
            530                 535                 540
Thr Ala Thr Ser Asn Glu Ile Lys Glu Ser Pro Leu His Gly Thr Gln
545                 550                 555                 560

Asn Thr Ile Asn Lys Arg Thr Gln Pro Thr Phe Gly Phe Thr Val Asn
                565                 570                 575

Trp Lys Phe Ser Glu
            580

<210> SEQ ID NO 25
<211> LENGTH: 1746
<212> TYPE: DNA
<213> ORGANISM: Gallus gallus

<400> SEQUENCE: 25
atggtgcacg caacctcccc gctgctgctg ctgctgctgc tcagcctggc tctggtggct     60
cccggcctct ctgccaggaa gaggacccag cccacctttg gcttcaccgt caattggaag    120
ttttcagagt ccaccactgt cttcacgggc agtgcttca tagacaggaa tgggaaggag     180
gtcctgaaga ccatgtggct gctgcggtca agtgttaatg acattggtga tgactggaaa    240
gctaccaggg tcggcatcaa catcttcact cgcctgcgca cacagaagga gggaggctcc    300
ggaggctccg ccagaaagtg ctcgctgact gggaaatgga ccaacgatct gggctccaac    360
atgaccatcg ggctgtgaa cagcagaggt gaattcacag cacctacat acagccgta      420 acagccacat caaatgagat caaagagtca ccactgcatg gacacaaaa caccatcaac    480 aagtccggcg gatccaccac tgtcttcacg gccagtgct tcatagacag gaatgggaag    540
gaggtcctga agaccatgtg gctgctgcgg tcaagtgtta atgacattgg tgatgactgg    600
aaagctacca gggtcggcat caacatcttc actcgcctgc gcacacagaa ggagggaggc    660
tccggaggct ccgccagaaa gtgctcgctg actgggaaat ggaccaacga tctgggctcc    720
aacatgacca tcgggctgt gaacagcaga ggtgaattca caggcaccta tcacagcc      780 gtaacagcca tcaaaatga atcaaagag tcaccactgc atgggacaca aacaccatc      840 aacaagagga cccagcccac ctttggcttc accgtcaatt ggaagttttc agagggaggt    900
tccggatcgg atccggctc tggcagcggc aggacccagc ccacctttgg cttcaccgtc    960
aattggaagt tttcagagtc caccactgtc ttcacgggcc agtgcttcat agacaggaat   1020
gggaaggagg tcctgaagac catgtggctg ctgcggtcaa gtgttaatga cattggtgat   1080
gactggaaag ctaccagggt cggcatcaac atcttcactc gcctgcgcac acagaaggag   1140
ggaggctccg gaggctccgc cagaaagtgc tcgctgactg ggaaatggac caacgatctg   1200
ggctccaaca tgaccatcgg gctgtgaac agcagaggtg aattcacagg cacctacatc   1260
acagccgtaa cagccacatc aaatgagatc aaagagtcac actgcatgg acacaaaac    1320 accatcaaca agtccggcgg atccaccact gtcttcacgg ccagtgcttc atagacagg   1380 aatgggaagg aggtcctgaa gaccatgtgg ctgctgcggt caagtgttaa tgacattggt   1440
gatgactgga agctaccag gtcggcatc aacatcttca ctcgcctgcg cacacagaag   1500
gagggaggct ccggaggctc cgccagaaag tgctcgctga ctgggaaatg gaccaacgat   1560
ctgggctcca acatgaccat cggggctgtg aacagcagag gtgaattcac aggcacctac   1620
atcacagccg taacagccac atcaaatgag atcaaagagt caccactgca tgggacacaa   1680
aacaccatca acaagaggac ccagcccacc tttggcttca ccgtcaattg gaagttttca   1740
gagtga                                                             1746
```

<210> SEQ ID NO 26
<211> LENGTH: 897
<212> TYPE: DNA
<213> ORGANISM: Gallus gallus

<400> SEQUENCE: 26

```
atggtgcacg caacctcccc gctgctgctg ctgctgctgc tcagcctggc tctggtggct      60
cccggcctct ctgccaggaa gaggacccag cccacctttg gcttcaccgt caattggaag     120
ttttcagagt ccaccactgt cttcacgggc cagtgcttca tagacaggaa tgggaaggag     180
gtcctgaaga ccatgtggct gctgcggtca agtgttaatg acattggtga tgactggaaa     240
gctaccaggg tcggcatcaa catcttcact cgcctgcgca cacagaagga gggaggctcc     300
ggaggctccg ccagaaagtg ctcgctgact gggaaatgga ccaacgatct gggctccaac     360
atgaccatcg gggctgtgaa cagcagaggt gaattcacag gcacctacat cacagccgta     420
acagccacat caaatgagat caaagagtca ccactgcatg ggacacaaaa caccatcaac     480
aagtccggcg atccaccac tgtcttcacg gccagtgct tcatagacag gaatgggaag      540
gaggtcctga agaccatgtg gctgctgcgg tcaagtgtta atgacattgg tgatgactgg     600
aaagctacca gggtcggcat caacatcttc actcgcctgc gcacacagaa ggagggaggc     660
tccggaggct ccgccagaaa gtgctcgctg actgggaaat ggaccaacga tctgggctcc     720
aacatgacca tcggggctgt gaacagcaga ggtgaattca caggcaccta tcacagcc      780
gtaacagcca tcaaatga gatcaaagag tcaccactgc atgggacaca aaacaccatc     840
aacaaggaga cccagcccac ctttggcttc accgtcaatt ggaagttttc agagtga       897
```

<210> SEQ ID NO 27
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 27

```
aatttaagct tatgttacgg ctgtgatgta g                                     31
```

<210> SEQ ID NO 28
<211> LENGTH: 290
<212> TYPE: PRT
<213> ORGANISM: Gallus gallus

<400> SEQUENCE: 28

```
Met Asn Lys Pro Ser Lys Phe Ala Leu Pro Leu Ala Phe Ala Ala Val
  1               5                  10                  15

Thr Ala Ser Gly Val Ala Ser Ala Gly Thr Gln Pro Thr Phe Gly Phe
                 20                  25                  30

Thr Val Asn Trp Lys Phe Ser Glu Ser Thr Thr Val Phe Thr Gly Gln
             35                  40                  45

Cys Phe Ile Asp Arg Asn Gly Lys Glu Val Leu Lys Thr Met Trp Leu
         50                  55                  60

Leu Arg Ser Ser Val Asn Asp Ile Gly Asp Asp Trp Lys Ala Thr Arg
 65                  70                  75                  80

Val Gly Ile Asn Ile Phe Thr Arg Leu Arg Thr Gln Lys Glu Gly Gly
                 85                  90                  95

Ser Gly Gly Ser Ala Arg Lys Cys Ser Leu Thr Gly Lys Trp Thr Asn
            100                 105                 110

Asp Leu Gly Ser Asn Met Thr Ile Gly Ala Val Asn Ser Arg Gly Glu
```

```
                    115                 120                 125
Phe Thr Gly Thr Tyr Ile Thr Ala Val Thr Ala Thr Ser Asn Glu Ile
    130                 135                 140
Lys Glu Ser Pro Leu His Gly Thr Gln Asn Thr Ile Asn Lys Ser Gly
145                 150                 155                 160
Gly Ser Lys Glu Ser Pro Leu His Gly Thr Gln Asn Thr Ile Asn Lys
                165                 170                 175
Arg Thr Gln Pro Thr Phe Gly Phe Thr Val Asn Trp Lys Phe Ser Glu
            180                 185                 190
Ser Thr Thr Val Phe Thr Gly Gln Cys Phe Ile Asp Arg Asn Gly Lys
        195                 200                 205
Glu Val Leu Lys Thr Met Trp Leu Leu Arg Ser Ser Val Asn Asp Ile
    210                 215                 220
Gly Asp Asp Trp Lys Ala Thr Arg Val Gly Ile Asn Ile Phe Thr Arg
225                 230                 235                 240
Leu Arg Thr Gln Lys Glu Gly Gly Ser Gly Gly Ser Ala Arg Lys Cys
                245                 250                 255
Ser Leu Thr Gly Lys Trp Thr Asn Asp Leu Gly Ser Asn Met Thr Ile
            260                 265                 270
Gly Ala Val Asn Ser Arg Gly Glu Phe Thr Gly Thr Tyr Ile Thr Ala
        275                 280                 285
Val Thr
    290

<210> SEQ ID NO 29
<211> LENGTH: 873
<212> TYPE: DNA
<213> ORGANISM: Gallus gallus

<400> SEQUENCE: 29
atgaacaaac cctccaaatt cgctctgccg cttgccttcg ccgccgttac ggcctctggt      60
gttgcctcgg ctggtaccca gcccaccttt ggcttcaccg tcaattggaa gttttcagag     120
tccaccactg tcttcacggg ccagtgcttc atagacagga atgggaagga ggtcctgaag     180
accatgtggc tgctgcggtc aagtgttaat gacattggtg atgactggaa agctaccagg     240
gtcggcatca acatcttcac tcgcctgcgc acacagaagg agggaggctc cggaggctcc     300
gccagaaagt gctcgctgac tgggaaatgg accaacgatc tgggctccaa catgaccatc     360
ggggctgtga acagcagagg tgaattcaca ggcacctaca tcacagccgt aacagccaca     420
tcaaatgaga tcaaagagtc caccactgca tgggacacaa acaccatcaa caagtccggc     480
ggatccaaag agtcaccact gcatgggaca caaaacacca tcaacaagag acccagcccc     540
acctttggct tcaccgtcaa ttggaagttt tcagagtcca ccactgtctt cacgggccag     600
tgcttcatag acaggaatgg gaaggaggtc ctgaagacca tgtggctgct gcggtcaagt     660
gttaatgaca ttggtgatga ctggaaagct accagggtcg gcatcaacat cttcactcgc     720
ctgcgcacac agaaggaggg aggctccgga ggctccgcca gaaagtgctc gctgactggg     780
aaatggacca acgatctggg ctccaacatg accatcgggg ctgtgaacag cagaggtgaa     840
ttcacaggca cctacatcac agccgtaaca taa                                  873

<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence: Synthetic
```

```
peptide

<400> SEQUENCE: 30

Ser Gly Gly Ser
  1

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Gly Ser Gly Ser Gly Ser Gly Ser Gly Ser Gly
  1               5                  10

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Gly Ser Gly Ser Gly Ser
  1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Ser Gly Ser Gly Ser Gly
  1               5
```